United States Patent
Amin et al.

(10) Patent No.: US 9,211,539 B2
(45) Date of Patent: Dec. 15, 2015

(54) VARIABLE VOLUME MIXING AND AUTOMATIC FLUID MANAGEMENT FOR PROGRAMMABLE MICROFLUIDS

(75) Inventors: Ahmed Mohamed Eid Amin, Wheeling, IL (US); Han-Sheng Chuang, Taipei (TW); Steven T. Wereley, West Lafayette, IN (US); Mithuna Shamabhat Thottethodi, Bellevue, WA (US); Terani Nadadoor Vijaykumar, West Lafayette, IN (US); Stephen C. Jacobson, Bloomington, IN (US)

(73) Assignee: Purdue Research Foundation, West Lafayette, IN (US)

( * ) Notice: Subject to any disclaimer, the term of this patent is extended or adjusted under 35 U.S.C. 154(b) by 1034 days.

(21) Appl. No.: 13/262,664

(22) PCT Filed: Apr. 2, 2010

(86) PCT No.: PCT/US2010/029808
§ 371 (c)(1),
(2), (4) Date: Jan. 24, 2012

(87) PCT Pub. No.: WO2010/115123
PCT Pub. Date: Oct. 7, 2010

(65) Prior Publication Data
US 2012/0136492 A1    May 31, 2012

Related U.S. Application Data

(60) Provisional application No. 61/165,942, filed on Apr. 2, 2009.

(51) Int. Cl.
*G05D 7/00* (2006.01)
*B01L 3/00* (2006.01)
*B01F 5/10* (2006.01)
*B01F 13/00* (2006.01)

(Continued)

(52) U.S. Cl.
CPC ........... *B01L 3/502784* (2013.01); *B01F 5/102* (2013.01); *B01F 5/108* (2013.01);
(Continued)

(58) Field of Classification Search
CPC .................. B01F 5/102; B01F 13/0059; B01L 2400/0481; B01L 2400/0633; B01L 3/502784; G01N 35/08; G01N 2035/00544
USPC ......................................... 700/285
See application file for complete search history.

(56) References Cited

U.S. PATENT DOCUMENTS 6,275,245 B1 * 8/2001 Wen et al. ................. 346/140.1
7,054,719 B2 * 5/2006 Pham et al. ................ 700/265

(Continued)

*Primary Examiner* — Robert Fennema
*Assistant Examiner* — Sivalingam Sivanesan
(74) *Attorney, Agent, or Firm* — Maginot, Moore & Beck, LLP

(57) ABSTRACT

A microfluidic arrangement including a fluid channel configured to receive a first fluid from a first inlet and a second fluid from a second inlet, and a mixer connected to the fluid channel, the mixer including a mixer channel configured to receive a volume of the first fluid and a volume of the second fluid from the fluid channel, the mixer channel defining a mixer capacity, wherein the mixer is (i) configured to mix the volume of the first fluid and the volume of the second fluid in order to provide a mixture of the first fluid and the second fluid when the combined volume of the first fluid and the second fluid is less than the mixer capacity, and (ii) further configured to mix the volume of the first fluid and the volume of the second fluid in order to provide a mixture of the first fluid and the second fluid when the combined volume of the first fluid and the second fluid is equal to the mixer capacity.

16 Claims, 24 Drawing Sheets

(51) Int. Cl.
*G01N 35/08* (2006.01)
*G01N 35/00* (2006.01)

(52) U.S. Cl.
CPC ....... *B01F13/0059* (2013.01); *B01L 3/502723* (2013.01); *B01L 2200/0605* (2013.01); *B01L 2300/0816* (2013.01); *B01L 2300/0867* (2013.01); *B01L 2300/0883* (2013.01); *B01L 2300/1827* (2013.01); *B01L 2400/0481* (2013.01); *B01L 2400/0633* (2013.01); *G01N 35/08* (2013.01); *G01N 2035/00544* (2013.01); *Y10T 137/0318* (2015.04); *Y10T 137/85978* (2015.04)

(56) References Cited

U.S. PATENT DOCUMENTS

| | | | | |
|---|---|---|---|---|
| 8,075,852 | B2* | 12/2011 | Gao et al. | 422/502 |
| 8,557,518 | B2* | 10/2013 | Jovanovich et al. | 435/6.1 |
| 8,578,389 | B1* | 11/2013 | Boucher | 718/106 |
| 2003/0040105 | A1* | 2/2003 | Sklar et al. | 435/287.2 |
| 2006/0280029 | A1* | 12/2006 | Garstecki et al. | 366/336 |
| 2007/0267335 | A1* | 11/2007 | Gao et al. | 210/120 |
| 2008/0118369 | A1* | 5/2008 | Sando et al. | 417/36 |
| 2008/0131327 | A1* | 6/2008 | Van Dam et al. | 422/103 |
| 2009/0145485 | A1* | 6/2009 | Smith et al. | 137/2 |
| 2012/0309648 | A1* | 12/2012 | Tseng et al. | 506/11 |

* cited by examiner

VARIABLE VOLUME MIXING AND AUTOMATIC FLUID MANAGEMENT FOR PROGRAMMABLE MICROFLUIDS

PRIORITY

This application is a U.S. National Stage Application of International Patent Application PCT/US2010/029808, titled Variable Volume Mixing and Automatic Fluid Management For Programmable Microfluids, filed 2 Apr. 2010, which claims priority to U.S. Provisional patent Application No. 61/165,942, filed Apr. 2, 2009, each of which is incorporated herein by reference.

CROSS-REFERENCE TO RELATED APPLICATIONS

This application claims priority from U.S. Provisional Patent Application No. 61/165,942, filed Apr. 2, 2009, the contents of which are incorporated herein by reference in their entirety.

STATEMENT REGARDING FEDERALLY SPONSORED RESEARCH OR DEVELOPMENT

This invention was made with government support under the grant numbers CCF-0726821 and CCF-0726694 awarded by National Science Foundation. The government has certain rights in the invention.

FIELD

This application relates to the field of microfluidics and particularly to a method and apparatus for programmable control of mixing and metering fluids in microfluidics.

BACKGROUND

Advances in microfluidic research has enabled lab-on-a-chip (LoC) technology to achieve miniaturization and integration of biological and chemical analyses to a single chip comprising channels, valves, mixers, heaters, separators, and sensors. These miniature instruments offer the rare combination of faster, cheaper, and higher-precision analyses in comparison to conventional bench-scale methods. LoCs have been applied to diverse domains such as proteomics, genomics, biochemistry, virology, cell biology, and chemical synthesis. However, to date LoCs have been designed as application-specific chips, which incurs significant design effort, turn-around time, and cost, and degrades designer and user productivity.

A significant operation in almost all assays performed on LoCs is the mixing of one or more fluids. Typically, assay protocols dictate that fluids are mixed in certain ratios, and, in some cases, in certain absolute volumes. To achieve different mixing ratios, current LoCs typically employ input channels of different dimensions, where the ratio of the dimensions is equal to the desired mixing ratio outcome. These channels then feed into a common, larger channel where mixing by diffusion takes place. To achieve variable volume mixing, current LoCs use external metering techniques to carefully measure the required fluid volumes prior to their mixing. In either case, the volume of each fluid used in the mixing process is variable.

Programmable LoCs (PLoCs) have been developed which are flexible and not limited to specific applications. These PLoCs are also capable of automatically conducting assays. In a PLoC, the assays are programmed in a high-level language and are compiled to automatically run on a general or multi-purpose microfluidic chip.

PLoCs have a general layout with a general set of microfluidic components. All channels have equal, fixed cross-sectional dimensions. Fluid flows in discrete volumes rather than in a continuous-flow approach. Therefore, the existing techniques to achieve variable ratio mixing cannot be applied to conventional PLoCs. Instead, current PLoC mixers must use a fixed volume approach to mixing where a mixer is completely filled with a defined total volume of two liquids before mixing can take place. Furthermore, because the fluids to be mixed in absolute volumes may be generated in intermediate assay steps, external fluid metering to achieve variable volume mixing is not possible. Accordingly, it would be desirable to provide a PLoC that is capable of variable volume mixing.

One issue with providing a variable volume mixing system in a PLoC mixing systems is the introduction of air bubbles into the mixer. Air bubbles can impede mixing efficiency by keeping two fluids separated from one another, thus inhibiting the mixing process. Accordingly, it would also be advantageous if such a variable volume PLoC mixing system were capable of effectively handling air bubbles in the mixer.

Yet another issue with mixing systems in PLoC arrangements is fluid volume management. The issue of fluid volume management arises because fluids have a fixed total volume, and the use of a fluid in one instance depletes the total volume, leaving less fluid for later uses of the fluid. If there are many uses of a fluid, the given volume of the fluid must be distributed carefully among the uses to prevent execution from running out of the fluid before all of the uses occur. This distribution poses a challenge when the uses require different proportions of volumes as is the case when a fluid is mixed with different other fluids in different ratios (e.g., one use for a fluid is in a mix ratio of 1:2 while another use for the same fluid is in a mix ratio of 1:10). Dealing with such distributions is further complicated by low-level, implementation-dependent details of the fluidic hardware, such as maximum capacity (of reservoirs and functional units) and minimum fluid transport resolution (imposed by the fluid transport/handling hardware). Forcing the programmer to handle these constraints would diminish the practicality of PLoCs. Consequently, it would be advantageous to handle this issue automatically using a combination of the compiler and run-time system.

One proposed method for dealing with fluid volume management issues is a reactive approach for volume management called regeneration. Regeneration allows the fluid to run out and re-generates the fluid just before the next use by re-executing the code fragments that produce the fluid (i.e., the backward slice). While elegant in theory, regeneration may place a high or unbounded demand on LoC resources. Repeating unbounded resources through virtualization is feasible in conventional computers, but microfluidic technology is not yet at that level of maturity. Even when regeneration is feasible, regeneration re-executes fluidic instructions (in the fluidic datapath) which are slow and are likely to incur overhead (PLoCs use a heterogeneous organization where the datapath is fluidic and control is electronic and orders-of-magnitude faster). In view of the foregoing, it would be desirable to provide a more pro-active approach to fluid volume management in order to reduce the chances of running out of a fluid. It would be advantageous if the improved method of fluid volume management could largely avoid regeneration's overhead but maintain some of the other advantages of regeneration.

Therefore, because of all the above stated shortcomings, it would be desirable to provide an improved apparatus and method for the transport and metering of variable volumes of fluids in a LoC arrangement.

SUMMARY

In one form thereof, a microfluidic arrangement is disclosed. The microfluidic arrangement includes a fluid channel configured to receive a first fluid from a first inlet and a second fluid from a second inlet, and a mixer connected to the fluid channel, the mixer including a mixer channel configured to receive a volume of the first fluid and a volume of the second fluid from the fluid channel, the mixer channel defining a mixer capacity, wherein the mixer is (i) configured to mix the volume of the first fluid and the volume of the second fluid in order to provide a mixture of the first fluid and the second fluid when the combined volume of the first fluid and the second fluid is less than the mixer capacity, and (ii) further configured to mix the volume of the first fluid and the volume of the second fluid in order to provide a mixture of the first fluid and the second fluid when the combined volume of the first fluid and the second fluid is equal to the mixer capacity.

In another form thereof, a method of mixing a first fluid and a second fluid in a programmable lab-on-a-chip (PLoC) arrangement is disclosed. The method includes transporting a first fluid to a mixer in the PLoC arrangement, the mixer having a mixer channel defining a mixer capacity, transporting a second fluid to the mixer, wherein the total combined volume of the first fluid and the second fluid is less than the mixer capacity, and mixing the first fluid and the second fluid within the mixer channel into a mixture of the first fluid and the second fluid.

The above described features and advantages, as well as others, will become more readily apparent to those of ordinary skill in the art by reference to the following detailed description and accompanying drawings. While it would be desirable to provide a microfluidics method and system that provides one or more of these or other advantageous features, the teachings disclosed herein extend to those embodiments which fall within the scope of the appended claims, regardless of whether they accomplish one or more of the above-mentioned advantages.

DESCRIPTION

General LoC Arrangement

Figure 1:
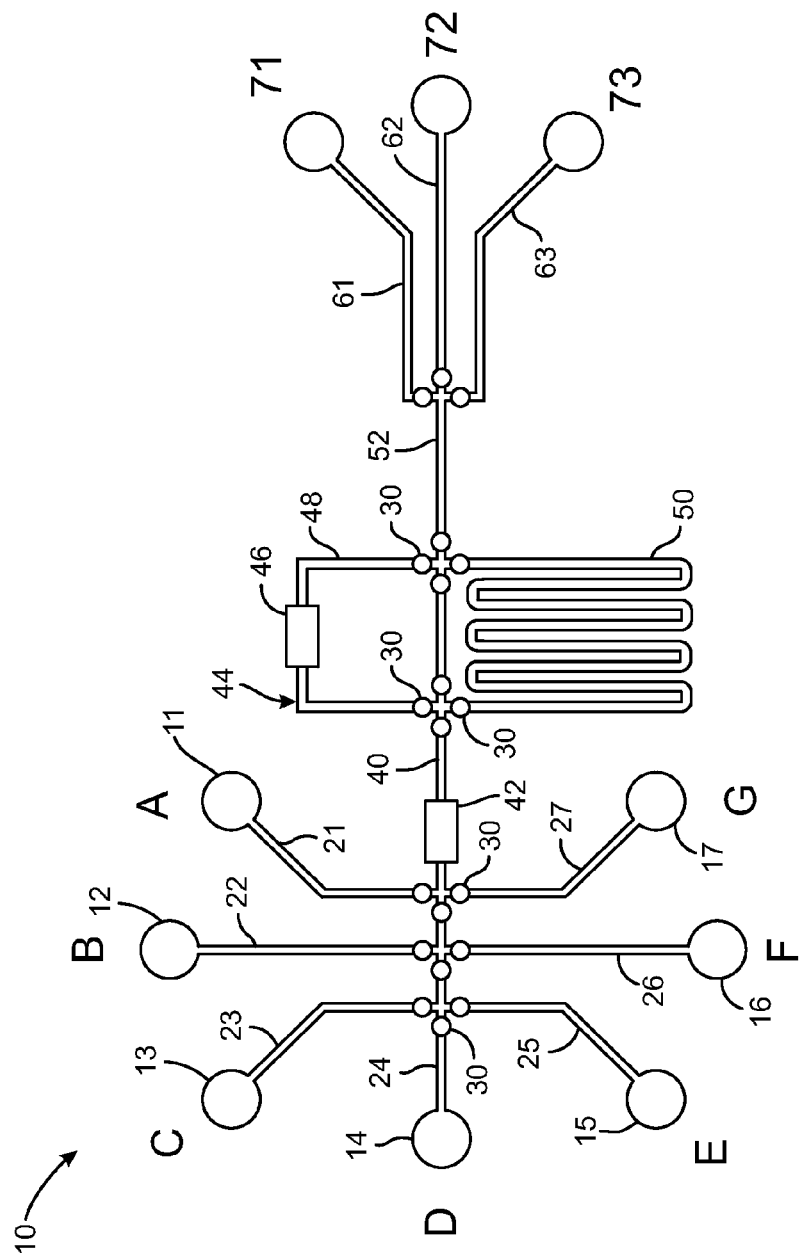
FIG. 1 is a schematic of a Programmable Lab on a Chip (PLoC) mask.

With reference to FIG. 1, an exemplary embodiment of a PLoC arrangement 10 with variable volume mixing and automatic fluid management is shown. The PLoC arrangement 10 includes a plurality of liquid storage reservoirs/sources 11-17 connected to a plurality of inlet channels 21-27. A plurality of valves 30 are positioned throughout the PLoC arrangement 10 to control the flow of fluid through the PLoC (individual valves are also noted herein as reference numeral 30). A first pump 42 is configured to draw fluid out of one of the liquid sources 11-17 and into a main channel 40. The PLoC arrangement 10 further comprises a mixing loop 44 with a second pump 46 in a mixing loop. The PLoC arrangement 10 also comprises a heating loop 50 and a sensing position 52. A plurality of liquid outlet channels 61-63 lead to liquid outlets/reservoirs 71-73. A controller (not shown) is also included on the PLoC 10. The controller is configured to automatically control operation of various components of the PLoC 10, including the valves 30 and pumps 42 and 46.

Each liquid storage source/reservoir 11-17 is configured to feed an associated liquid (identified as liquids A-G in FIG. 1) into the associated inlet channel 21-27, depending upon the configuration of the valves 30 and the operation of the pump 42. For example, when the valve 30 associated with liquid channel 21 is opened and the pump 42 is operating, liquid A is drawn from source/reservoir 11 through inlet channel 21 and into the main channel 40. Accordingly, any of the various liquids A-G may be drawn into the main channel 40 using the pump and an appropriate valve configuration. The liquids A-G are generally different types or concentrations of fluids, but may also be duplicates. For example, liquid G could be a back-up volume of liquid A. Furthermore, it will be recognized that although liquids A-G in source/reservoirs 11-17 are shown in the embodiment of FIG. 1, additional or fewer liquids may be provided in other embodiments with an associated number of reservoirs and input channels.

In the embodiment of FIG. 1, the first pump 42 used to transport a liquid into the main channel 40 is a microfluidic peristaltic pump. Such pumps are generally known in the art and may comprise three interlocking valves positioned in channel 40. When one of these valves is opened, a vacuum is created in the valve chamber. When the valve is closed, pressure is created in the valve chamber. Accordingly, the three valves operate in sequence such that vacuum and pressure are created at the right instance in order to move fluid through the pump using peristaltic action. The movement of fluid within the pump 42 also acts to force fluid contained within the tube 40 through the tube. Because each pump stroke transfers a fixed volume of fluid (equal to the volume of the valve chamber), variable volume metering can be achieved by varying the number of pump strokes.

The mixer 44 is provided as a side loop to the main channel 40. The mixer 44 comprises the second peristaltic pump 46 provided in a loop channel 48 with a valve 30 at the inlet to the loop channel 48 and another valve 30 at the outlet of the loop channel 48. As explained in further detail below, the mixer 44 is configured to perform variable volume mixing. The mixer 44 is also programmable and capable of performing the variable volume mixing in an automated fashion.

With continued reference to the embodiment of FIG. 1, the heating loop 50 is arranged in parallel with the mixing loop 48. In particular, the heating loop 50 is positioned on the opposite side of the main channel 40 from the mixing loop 48. A valve 30 is positioned at the inlet to the heating loop 50 and another valve 30 is positioned at the outlet to the heating loop 50. The valves may be controlled to allow fluid to flow into and out of the heating loop. Fluid flowing through the heating loop is heated by a heater (not shown). It will be recognized that although a heating loop 50 is shown in FIG. 1, the loop in other embodiments may be a cooling loop or other fluid control loop.

The fluid in the main channel 40 may sensed at the sensing position 52. Although one sensing position has been shown in FIG. 1, it will be recognized that additional sensing positions may be desirable. Furthermore, any of various sensing apparatus may be used to sense different fluid properties or positions. For example, alignment sensors may be used to detect the existence of fluid at a particular position. Other examples of sensors that may be used include colorometric sensors, florescent sensors, or any of various other sensors configured to detect certain chemical or biological properties. In the embodiment of FIG. 1, if an alignment sensor is positioned at the sensing position 52, the sensor may be used to provide feedback to the LoC arrangement 10 indicating that the desired fluid has indeed been delivered to the main channel 40, and has been moved past the mixer 44. As explained in further detail below, this information can then be used by the controller as an indication that the system is ready to proceed with a next step, such as opening and closing valves in order to move the fluid slug out of a particular portion of the LoC arrangement 10 and into another portion of the LoC arrangement.

After processing fluid from the main channel 40 using the mixer 44 and/or the heater 50, the fluid is directed into one of the outlet channels 61-63. The eventual destination of the fluid is controlled based upon the configuration of the valves 30 at the ends of the outlet channels and the operation of the first pump 40, which acts to move fluid through the main channel 40. For example, if the valve 30 at the end of outlet channel 61 is open, the pump 40 may be operated to direct the fluid into the outlet channel 61 and into the fluid reservoir 71. Fluid deposited in the reservoirs 71-73 is available for later use by other devices connected to the PLoC.

Mixer Operation

With reference now to FIGS. 2-8, a simplified version of the embodiment of FIG. 1 is shown in order to further explain the mixer 44 on the PLoC. In the embodiment of FIGS. 2-8, a PLoC arrangement 100 is shown with only two fluid reservoirs: reservoir 111 for fluid A, and reservoir 112 for fluid B. As explained in the following paragraphs, at the microfluidic scale, by forcing fluids to be adjacently aligned or by forcing them in the same space, the fluids will mix by diffusion. The time required to achieve a fully mixed, homogeneous resultant depends on the fluids in consideration. An active mixer can increase mixing speed and efficiency by agitating the fluids. One such method to achieve active mixing is by driving fluids in a closed loop channel using a peristaltic pump.

Figure 2:
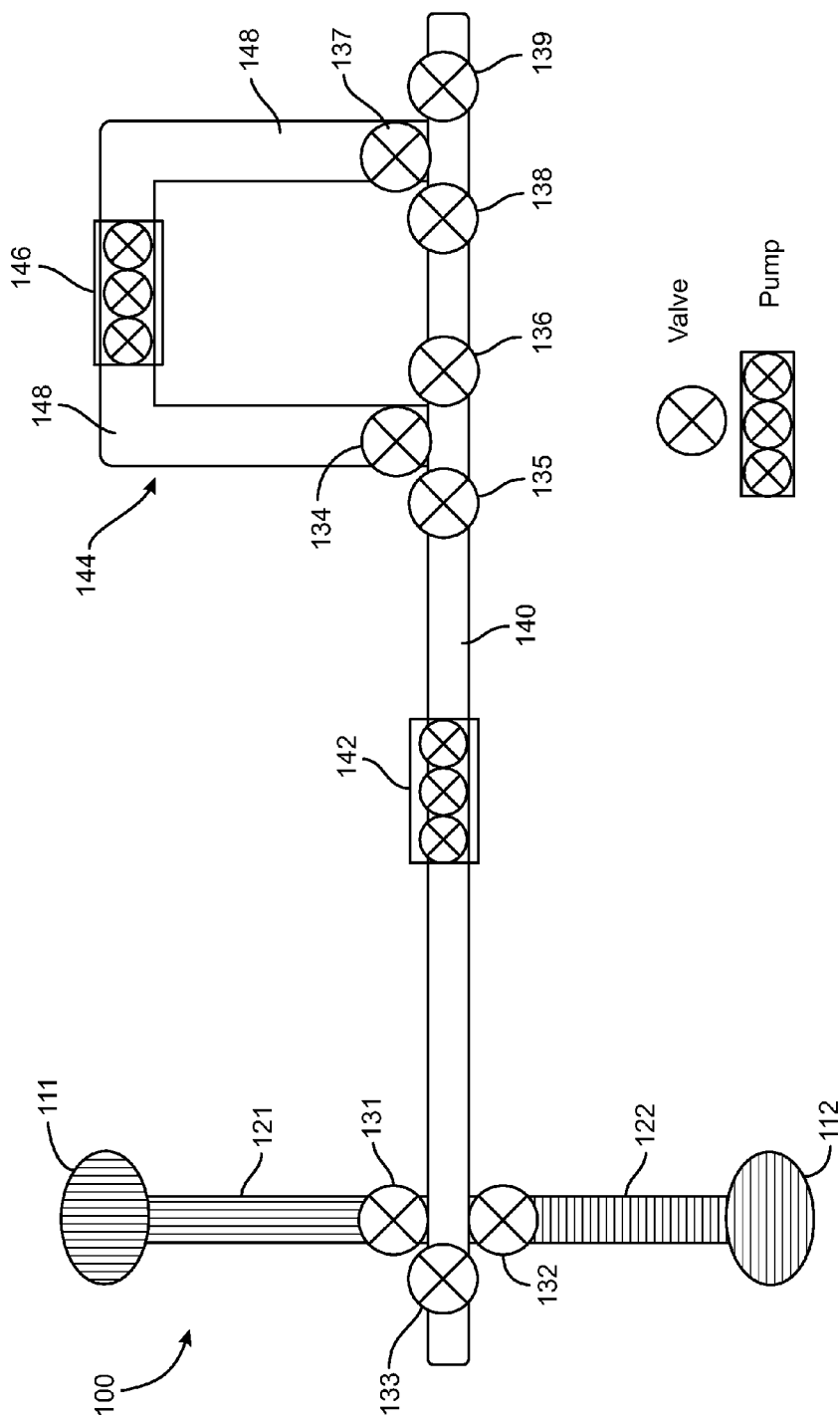
FIG. 2 is a schematic of a PLoC with two fluids and a mixer.
Figure 3:
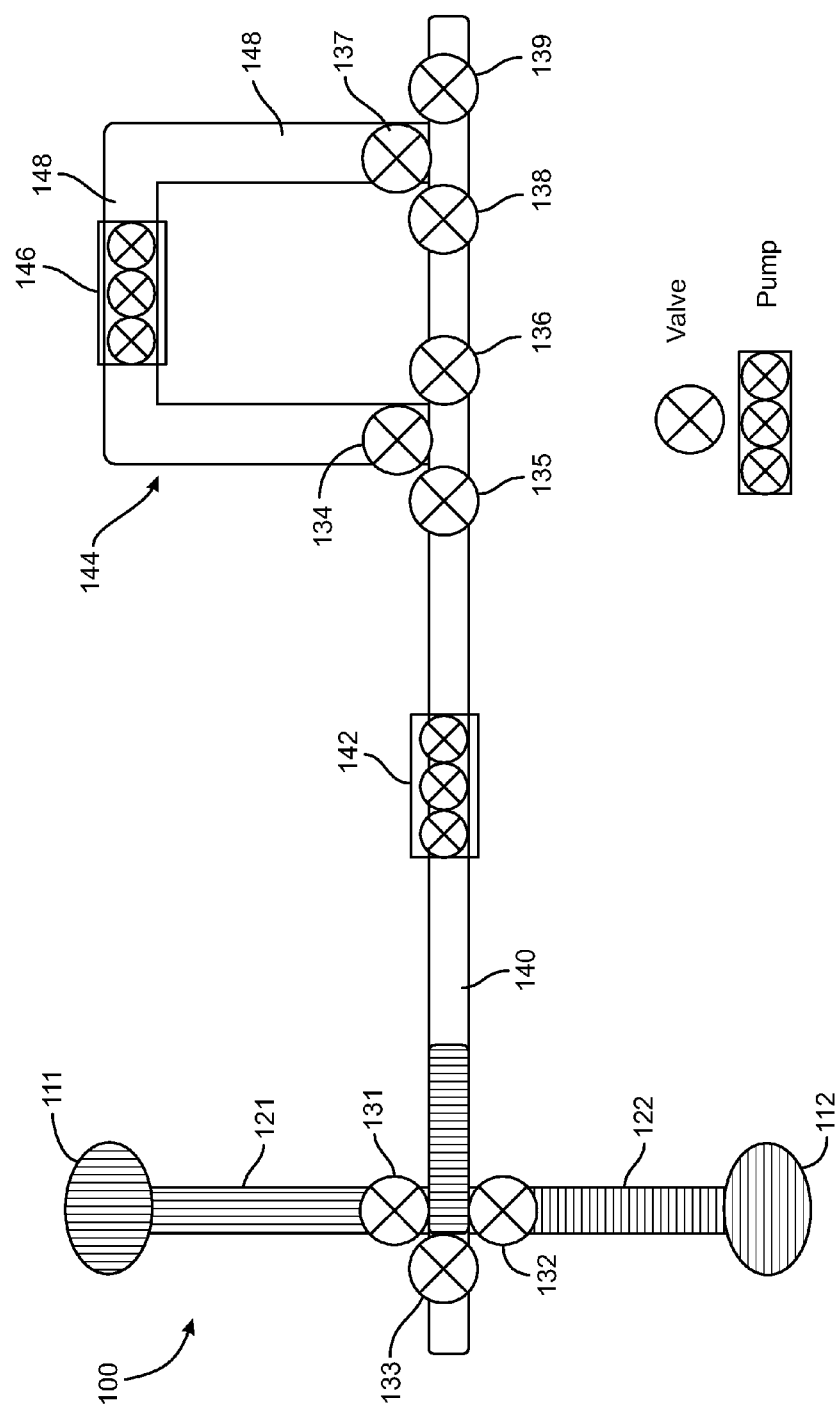
FIG. 3 is the schematic of FIG. 2 where fluid A is being metered.

With reference to FIGS. 2-8, mixing of the two fluids A and B in arbitrary volumes in a PLoC involves first transporting fluid A from its source 111 to the main channel 140. As shown in FIGS. 2 and 3, this is accomplished by opening valves 131, 135, 136, 138 and 139 and closing all other valves. The pump 142 is then activated, such that fluid is drawn from the source 111, through the inlet channel 121, and into the main channel, as shown in FIG. 3.

Figure 4:
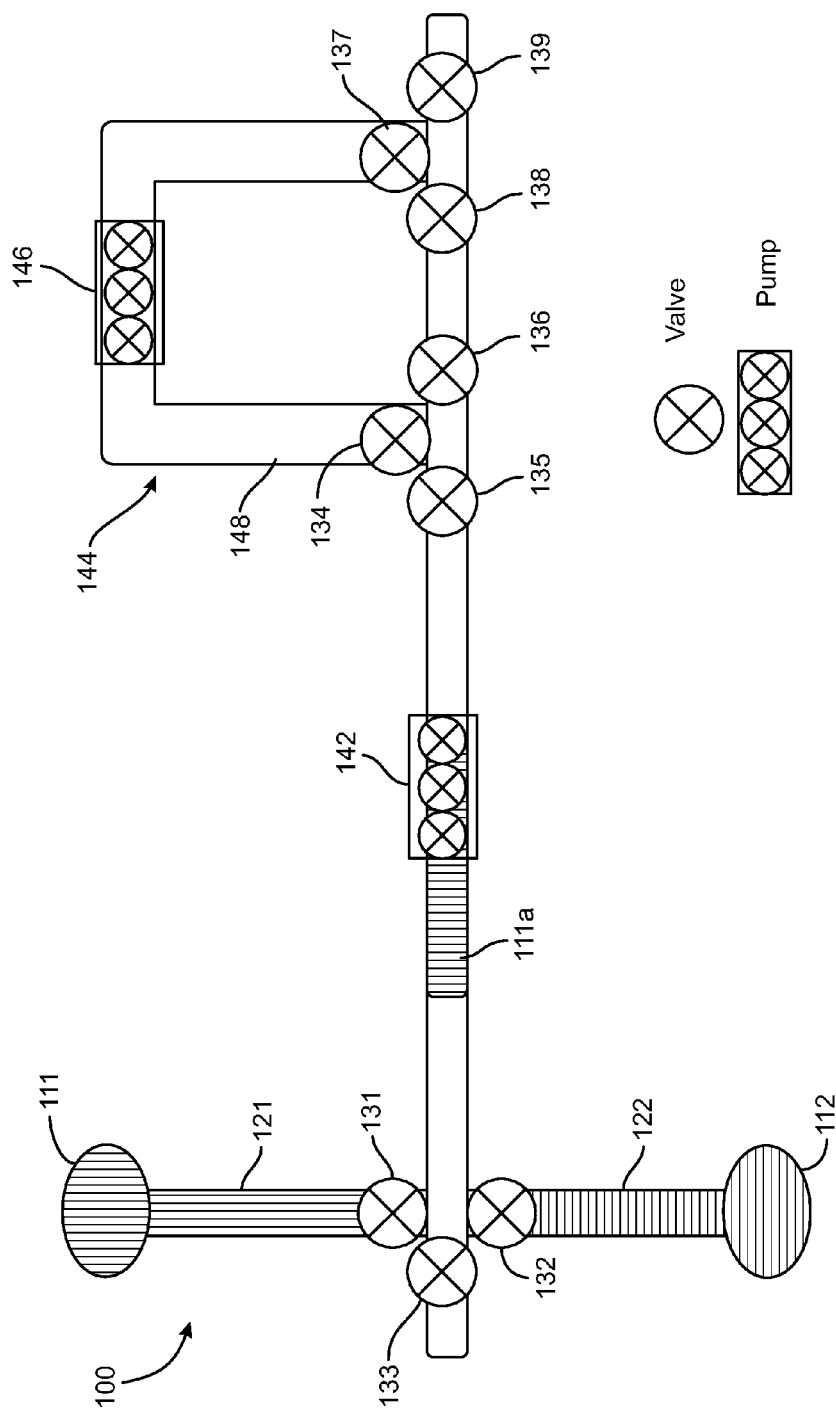
FIG. 4 is the schematic of FIG. 2 where the metered slug is transported across channel toward mixer.

The volume of fluid A drawn from the source 111 is metered to a desired volume. This is relatively simple to achieve with the peristaltic pump 142 by using a given number of pump strokes, since each pump stroke delivers a precise volume of fluid. As shown in FIG. 4, after the desired volume of fluid A is metered into the channel 140 (see metered slug 111a), valve 131 is closed to cut off further flow of fluid A into the channel 140. Valve 133 is then opened and the pump continues to operate in order to move the metered slug 111a of fluid A down the channel 140 and toward the mixer 144 (valves 135, 136, 138 and 139 also remain open).

Figure 5:
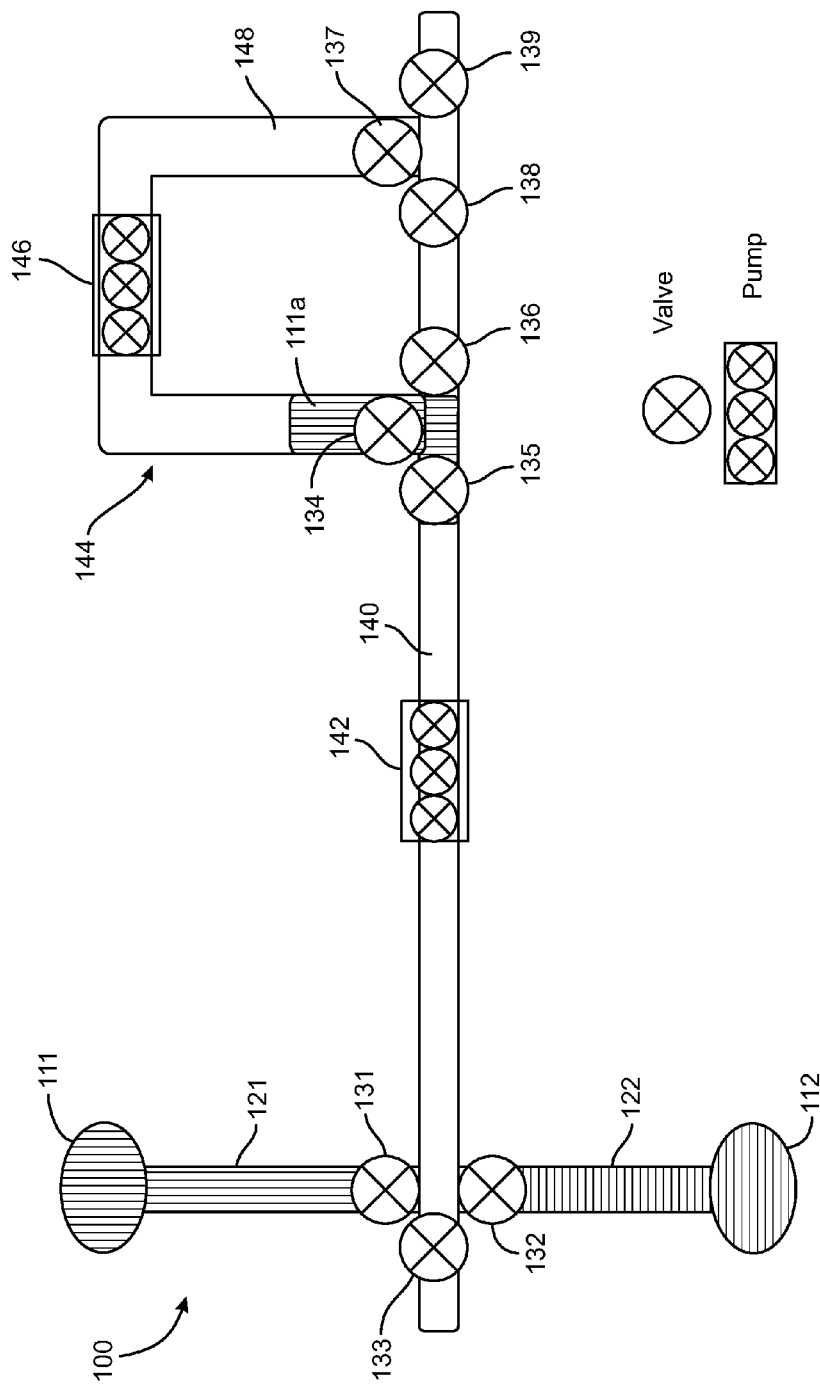
FIG. 5 is the schematic of FIG. 2 where the metered slug is inserted into mixer using the exact same number of pump strokes used to meter the slug.

As the slug 111a is moved toward the mixer 144, valves 136 and 138 are closed while valves 134 and 137 are opened (valves 133, 135, and 139 remain open). As shown in FIG. 5, this valve configuration allows the slug 111a to enter the mixing channel 148 of the mixer 144.

After the slug 111a of fluid A is fully positioned in the mixer 144, valves 134 and 137 are closed to trap the slug 111a in the mixer channel 148. A slug of fluid B may now be transported to the mixer 144 for mixing with the slug 111a of fluid A. The process for moving the slug of fluid B to the mixer is generally the same as that described above in FIGS. 2-5 for moving slug 111a to the mixer 144, with valve 132 being operated instead of valve 131 such that fluid B is released into the main channel 140.

Figure 6:
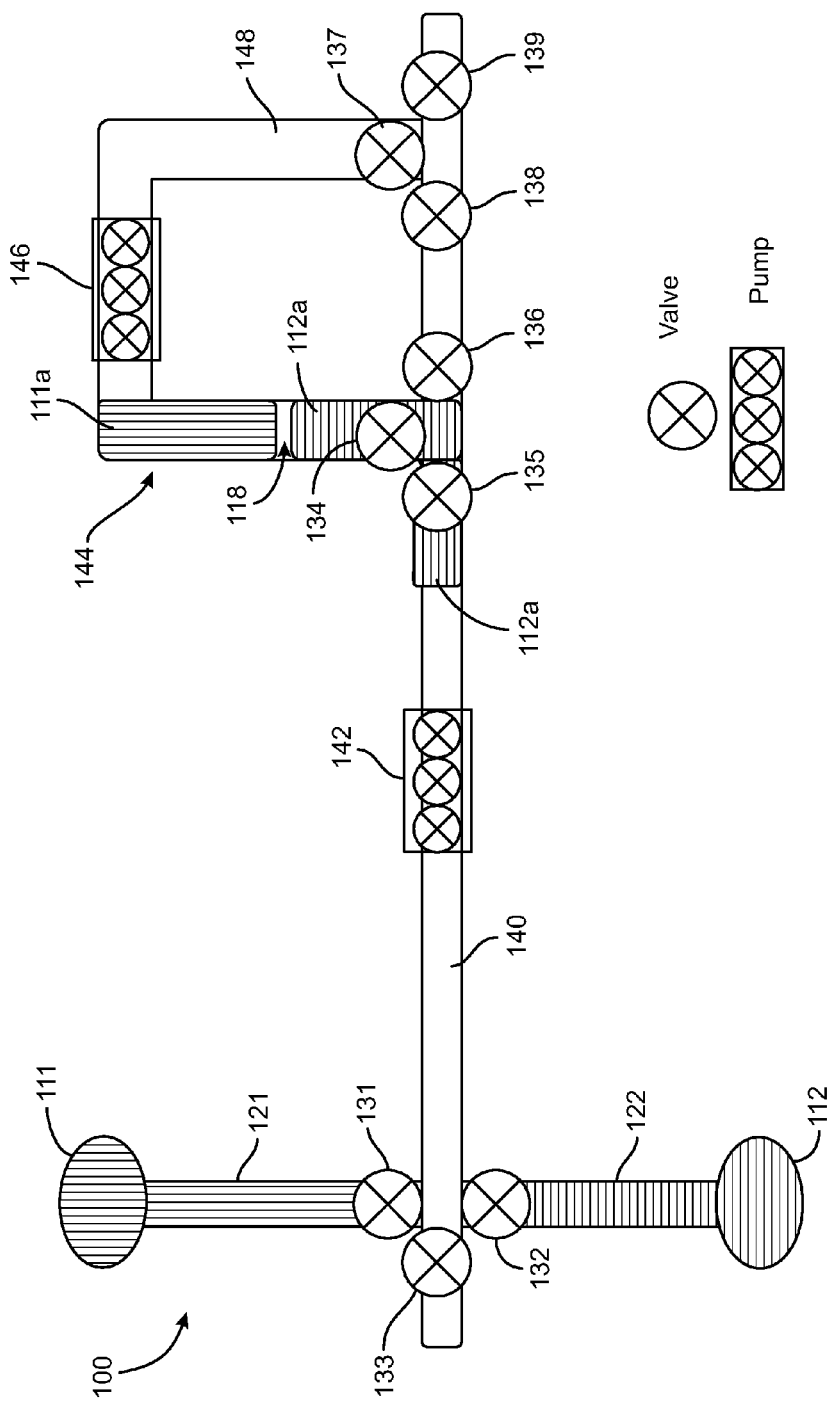
FIG. 6 is the schematic of FIG. 2 where fluid B is metered and the slug transported into mixer.

FIG. 6 shows a slug 112a of fluid B being transported into the mixer channel 148 where slug 111a is already located. When the slug 112a of fluid B is introduced into the mixer 144, one or more air bubbles 118 may be introduced between slug 111a and 112a.

Figure 7:
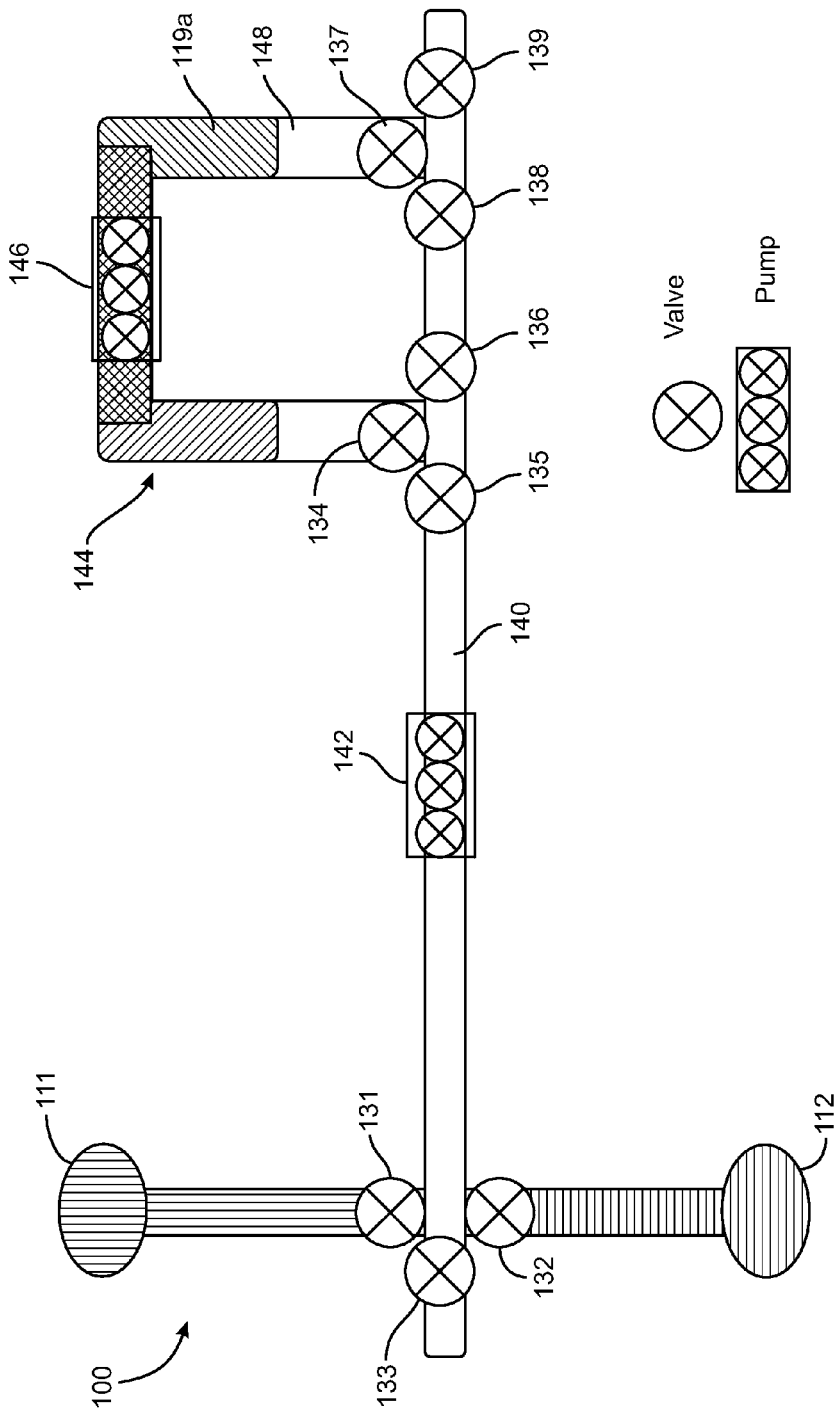
FIG. 7 is the schematic of FIG. 2 where mixer is sealed by closing external valves, and mixing commences by activating pump P2.
Figure 8:
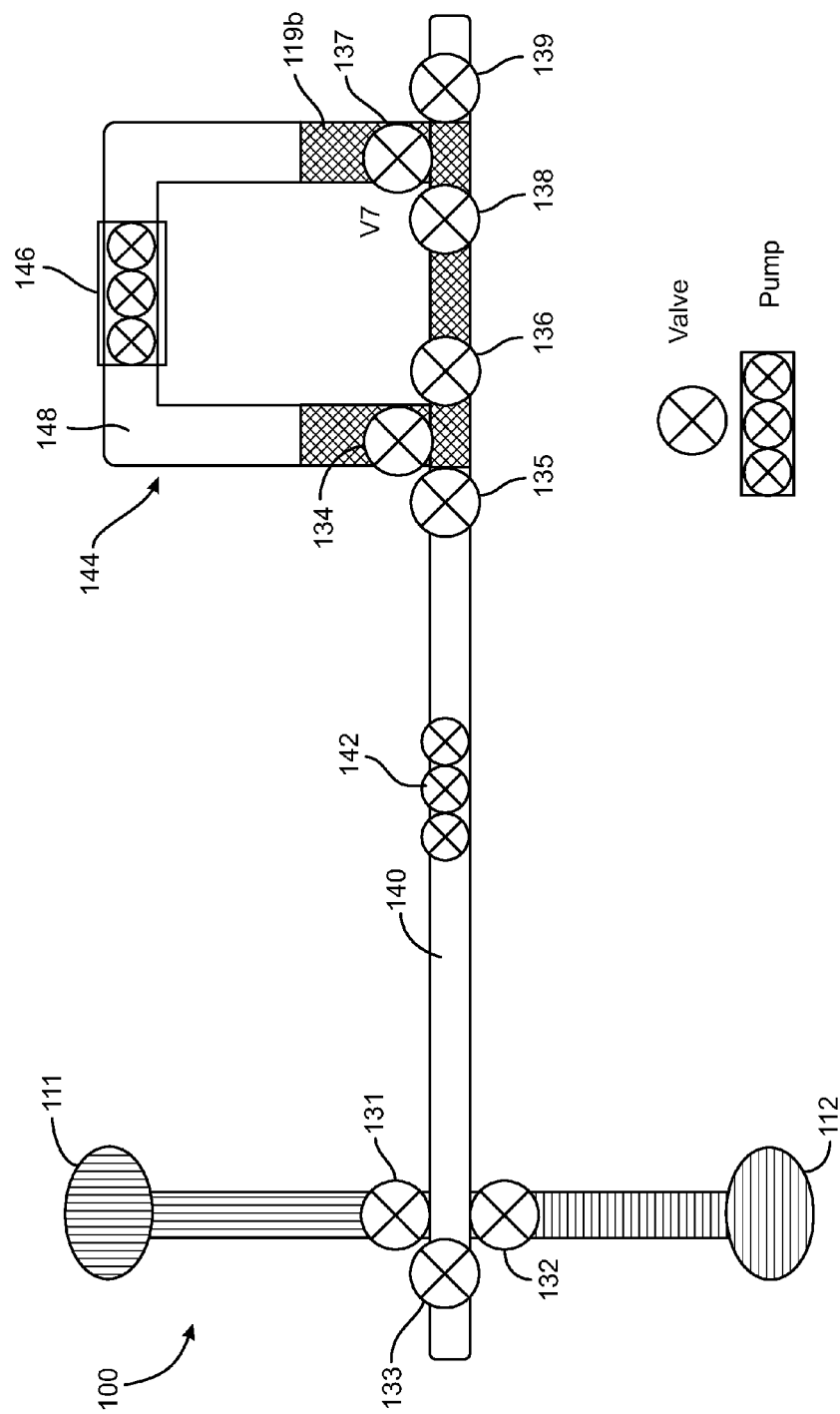
FIG. 8 is the schematic of FIG. 2 where mixing occurs after several loop iterations inside the mixer, mixing is complete and the resultant is a homogeneous mixture.

FIG. 7 shows mixing of the slugs of fluids A and B, 111a and 112a within the mixer 144. The mixing process is started by opening valves 134, 136, 137 and 138 and closing all other valves, creating a circular loop using the mixing channel 148. The two slugs 111a and 112a are then circulated in the mixing channel 148 using the peristaltic pump 146 in the mixer. The more pump iterations, the more homogeneous the resulting mixture. In FIG. 7, the partially combined slugs are represented by the diagonal lines 119a. FIG. 8 shows a homogeneous mixture 119b of the two slugs 111a and 112a in the mixing loop.

In order to achieve accurate arbitrary mix ratios it is desirable that a) the metered fluid slugs 111a and 112a enter the mixer 144 in their entirety, without any loss or residuals, and b) there is minimal or no air bubble 118 between the two fluid slugs 111a, 112a in the mixer. Small air bubbles will significantly reduce the efficiency of the mixing process. Larger air bubbles could completely prevent any mixing of the two slugs. Accordingly, embodiments of the PLoC arrangement 10 may include features to assist with slug alignment as well as air bubble removal, as discussed below under the related subheadings.

Using the embodiment of FIGS. 2-8, a PLoC is provided that is capable of variable volume mixing. In particular, the mixer 44 does not need to be completely filled in order to perform mixing (i.e., the total volume of fluids mixed in the channel does not need to be equal to the total mixer capacity defined by the mixing channel 48). Instead, a significant percentage of the mixer channel 48 may remain empty during the mixing process, as shown in FIGS. 7 and 8. Operation of the mixer 44 results in a homogeneous mixture of the fluids 111a and 112a mixed in the mixer channel 48 even though the combined volume of the mixed fluids is less than the mixer capacity. As discussed in further detail below, the PLoC arrangement includes various features to assist in such variable volume mixing, including fluid alignment features, and air bubble removal features.

Alignment of Metered Slug at Predetermined Positions

As mentioned previously, it is desirable to know the exact position of the slugs before, after or during execution of the variable mixing process. Therefore, accurate alignment of the metered slug at predetermined positions in the chip is necessary. For example, it is desirable to precisely align the fluid slug 112a at the entrance to the mixer 144 before pumping the slug 112a inside the mixer to prevent fluid from bypassing the mixer. It is also desirable to stop pumping the slug as soon as it has fully entered the mixer to make sure no air is pumped behind the slug. By ensuring the latter, air bubbles between consecutive slugs entering the mixer can be eliminated.

To achieve alignment at a specific location in the PLoC arrangement 100 (e.g., at the entrance of the mixer 144), one of at least three different control methods may be used in different embodiments of the PLoC arrangement. First, an open loop control system may be used which calculates the exact number of pump strokes required to transport a fluid from and to any points on the chip. The downside to this approach is that it requires extensive calibration of the pump 142. Because there is no feedback to the controller, minor variations (e.g., due to a highly viscous fluid or due to minor residuals already in the channels) will cause inaccuracies in the alignment.

Figure 9:
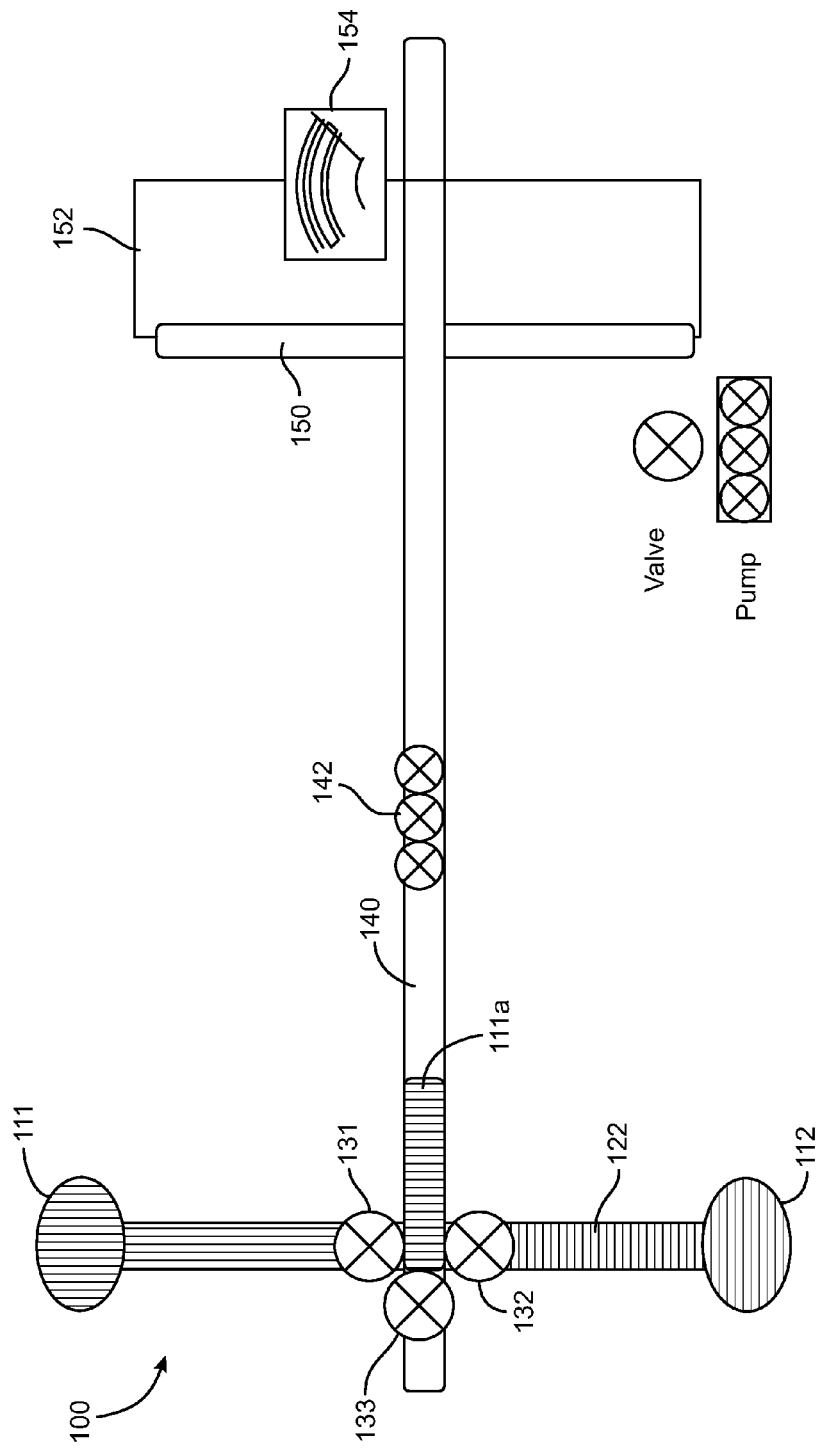
FIG. 9 is a schematic for measuring resistance where conductive polydimethylsiloxane (i.e., PDMS) is inserted at an alignment point and the resistance across terminals is measured.
Figure 10:
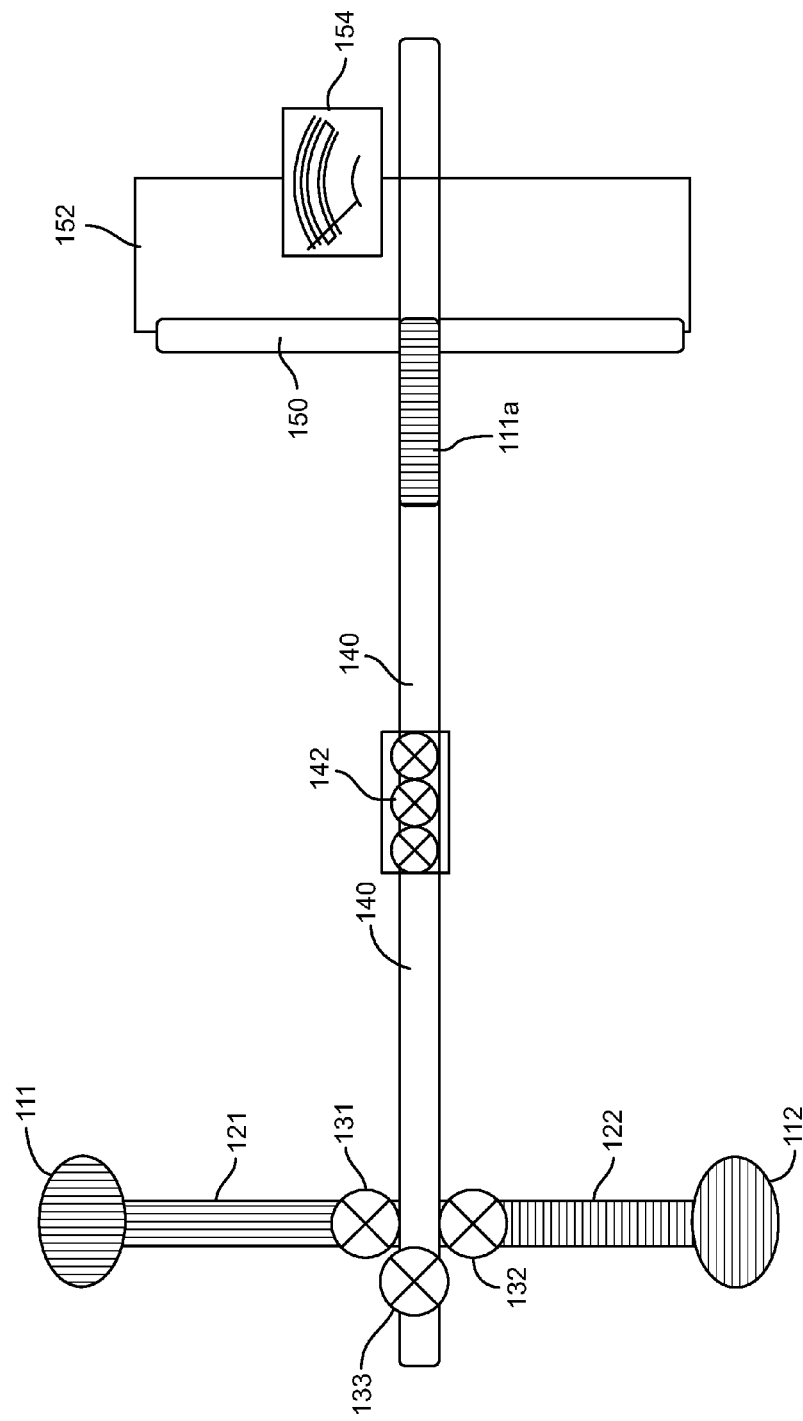
FIG. 10 is the schematic of FIG. 9, where a slug arrives at the alignment point, the fluid completes the circuit and thereby the measured resistance is reduced.

A second method for controlling fluid alignment is a closed loop system which detects whether a fluid slug has reached a certain point in the chip 100. Detection methods may include light/image sensors or electrical conductivity sensors. Sensors give different readings depending on the presence or lack of a fluid at various alignment points. The control system begins pumping the fluid while continuously monitoring the sensor reading. Once the fluid reaches the alignment point (i.e., the sensor), the pumping stops. One closed loop detection method involves the use of conductive PDMS (i.e., polydimethylsiloxane). Conductive PDMS is a material deposited at alignment points in the chip 100, such as the conductive PDMS material 150 shown in FIG. 9. The conductive material 150 is positioned on opposite sides of the channel 140 in a measurement circuit 152. Because the conductive material is removed from the channel 140, an open circuit is created such that ohmmeter 154 shows a very high resistance. However, as shown in FIG. 10, when a fluid slug (e.g., 111a) is positioned in the channel 140 at the location of the PDMS material 150, the fluid slug 111a acts as a conductor and completes the circuit 152. This results in a low resistance reading at ohmmeter 154. Therefore, by measuring the resistance across the terminals of the conductive PDMS, the control system can determine whether or not the fluid has reached the desired point.

A third method for controlling fluid alignment is an open loop system which utilizes a purge valve that allows air to pass while retaining fluid. By placing such valves at alignment points, the control system can use a large number of pump strokes to pump the fluid, while still guaranteeing that the fluid will not pass the purge valve. One embodiment of a purge valve is explained in further detail below under the subheading "Air Bubble Purging". However, it will be appreciated that other embodiments of purge valves are also possible.

Transport of Fluid into the Mixer

The foregoing paragraphs provide three examples of methods to align fluid in the channel 140. Alignment of fluid in the channel 140 is particularly helpful at the entrance to the mixer 144. In particular, by aligning a fluid slug at the entrance of the mixer 144, and then actuating the peristaltic pump 142 the same number of strokes used to initially meter the fluid, the entire slug is ensured to enter the mixer channel 148. Subsequent fluids that enter the mixer will have very small or no intervening air bubbles in between them. The same alignment methods can be used when transporting the resultant fluid out of the mixer. To meter an accurate volume of fluid, the contents of the mixer is aligned at a predetermined point prior to the metering, such that air volume does not contribute to the metered slug.

Figure 11:
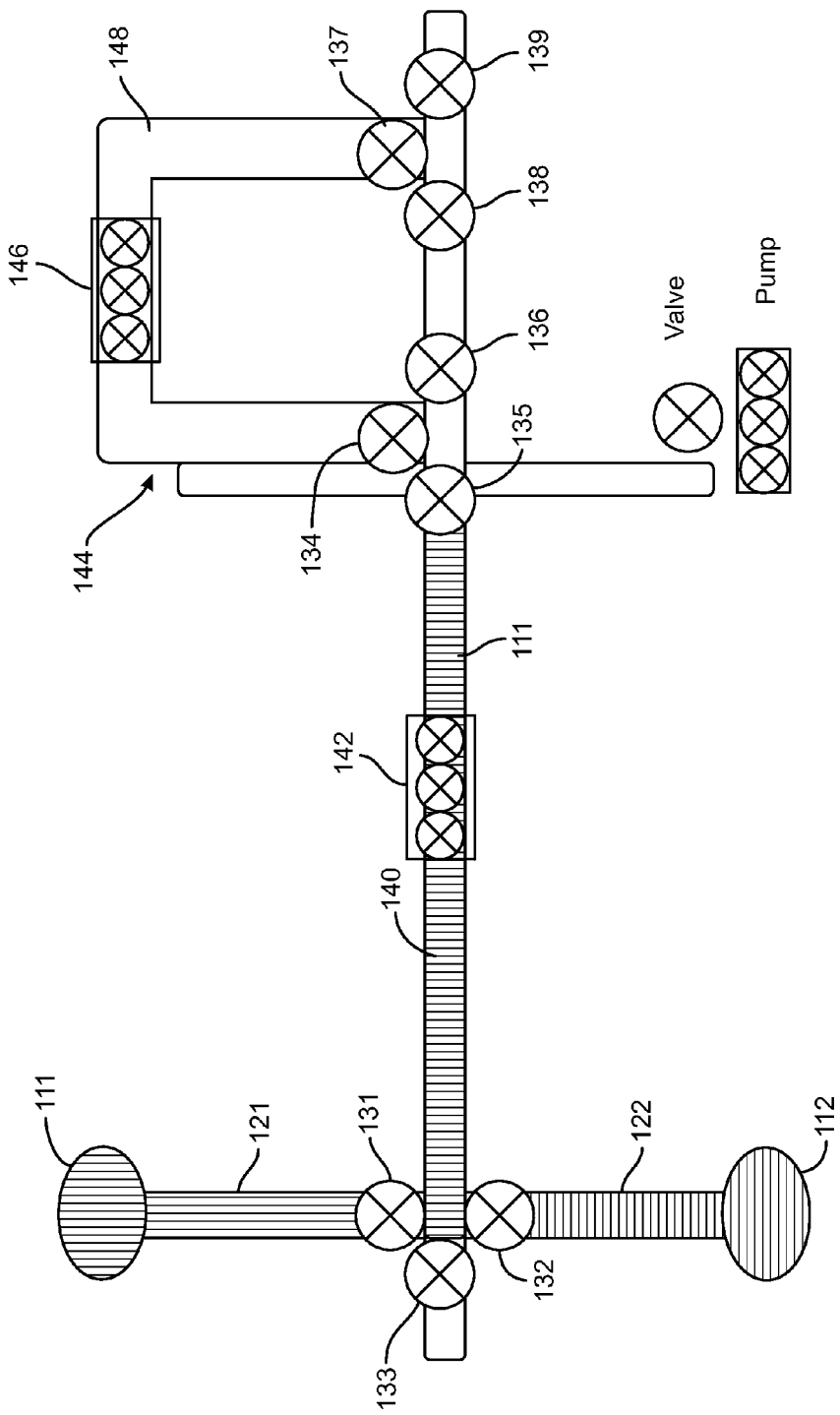
FIG. 11 is the schematic of an alternative embodiment to variable volume mixing, where the fluids are transported without metering to the alignment point (mixer entrance)
Figure 12:
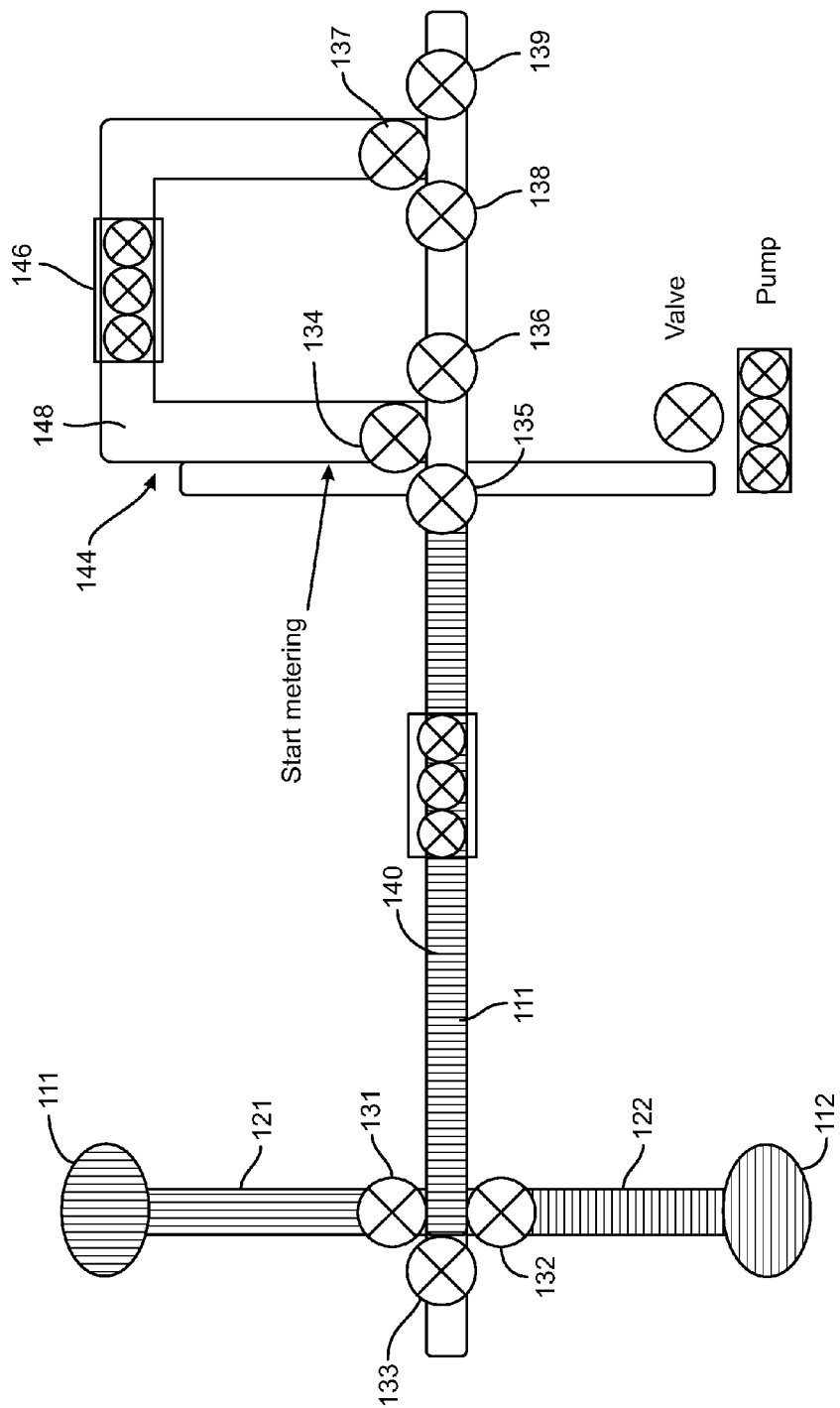
FIG. 12 is the schematic of FIG. 10, where after the fluid arrives at the mixer entrance, the required volume of the fluid is metered.
Figure 13:
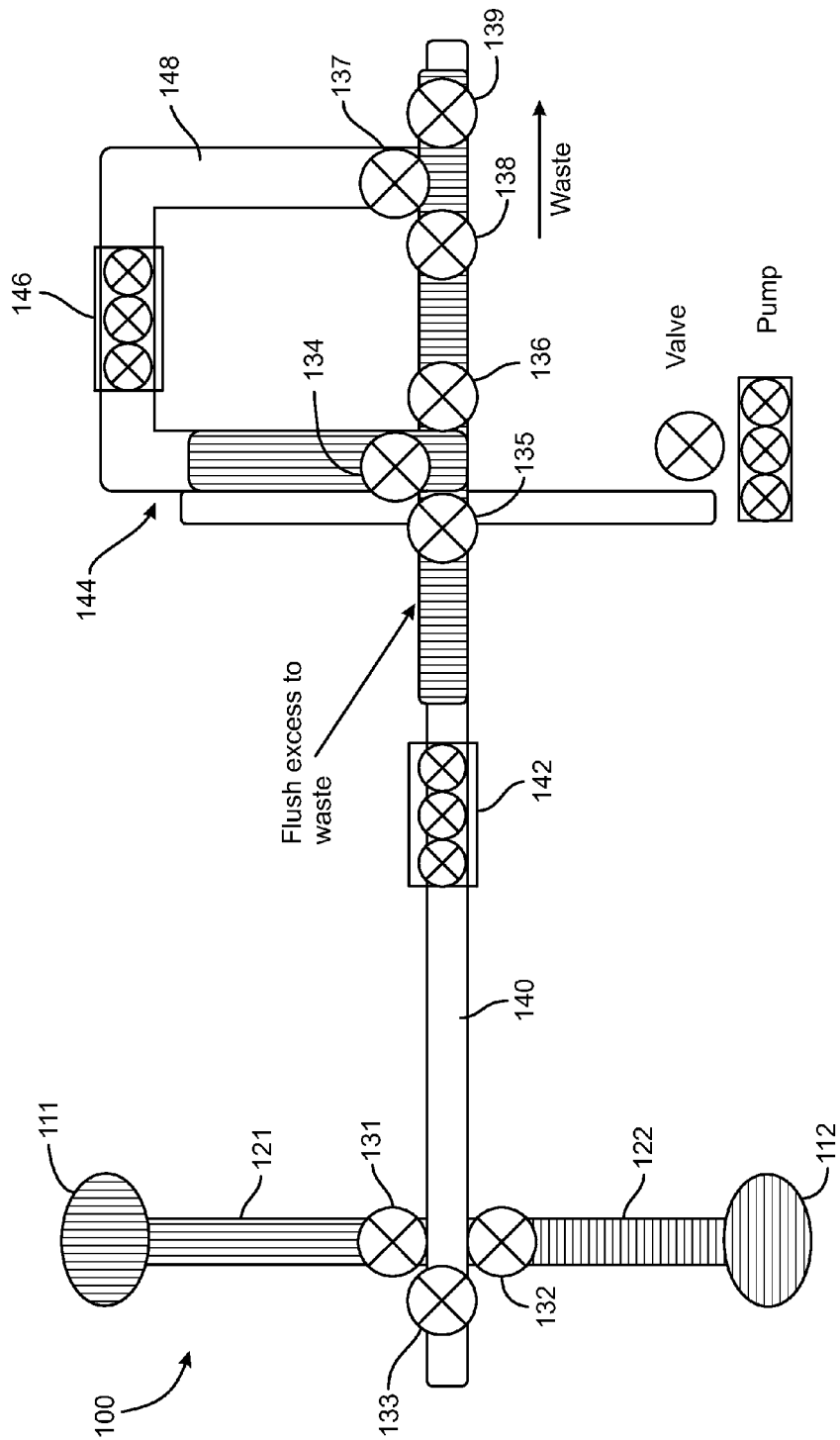
FIG. 13 is the schematic of FIG. 10, where once the required volume is metered, valves leading to mixer are closed and excess fluid is purged to waste, the same procedure is repeated for fluid B.

The above method involves first metering the fluid volume using a number of strokes proportional to the required fluid volume, and once the fluid is aligned at the entrance of the mixer, the same number of strokes is then used to force the entire slug into the mixer. This method has shown to be effective and also efficient, resulting in very little fluid waste. However, it will be recognized that other methods for metering fluid into the pump may be used. One alternative embodiment is shown in FIGS. 11-13. According to this embodiment, the fluid to be delivered to the mixer 144 is pumped continuously from its source until it reaches the entrance of the mixer, as shown in FIG. 11. Next, a predetermined number of pump strokes is actuated to achieve the desired slug volume (see FIG. 12). After that, the entrance to the mixer is shut off (i.e., valve 134 is closed), and any remaining fluid in the channel is purged to waste through open valves 135, 136, 138, and 139, as shown in FIG. 13. This alternative approach tends to be even more accurate in achieving the desired slug volume, but has the disadvantage of being more wasteful. One way to reduce waste is to return the unused fluid to its source rather than through waste via valve 139.

Air Bubble Purging

In the above embodiments it is desirable to minimize the occurrence of air bubbles between slugs (e.g., 111*a* and 112*a*) in the mixer. However, there may be cases (e.g., when using open loop calibration, as discussed above) when small air bubbles may still exist. In one embodiment, vents are provided in the mixer 144 that allow small air bubbles to be expelled from the mixer channel 148 in an orthogonal plane to the chip.

Figure 14:
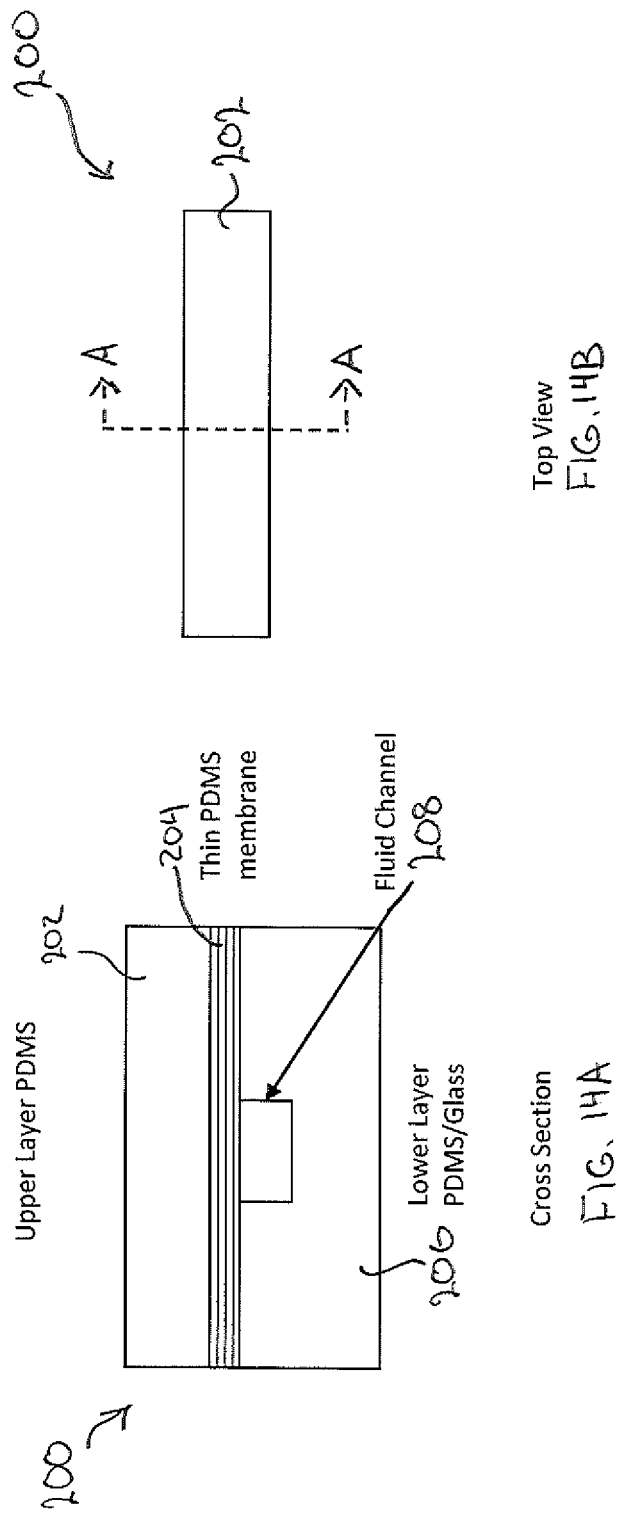
FIG. 14A shows cross section of a LoC arrangement with a fluid channel therein.
FIG. 14B shows a top view of the LoC of FIG. 14A with the cross-sectional position of FIG. 14A represented in dashed lines.

FIG. 14A shows a cross section of a fluidic LoC 200 without air vents, and FIG. 14B shows a top view of the fluidic LoC 200. The fluidic LoC 200 includes an upper layer 202 of PDMS material and a lower layer 206 of PDMS and glass material. A thin PDMS membrane 204 provides an intermediate layer that is positioned between the upper layer 202 and the lower layer 206. A fluid channel 208 is centrally positioned in the LoC 200. Although the top and bottom layers 202, 206 have been described herein as comprising a PDMS material, it will be recognized that different materials may be used in other embodiments. For example, a glass material could be used for the top and bottom layer. Also, PMMA (polymethyl methacrylate) or other polymers could also be used. In any event, the intermediate layer 104 will typically be comprised of a thin, flexible material such as PDMS.

Figure 15:
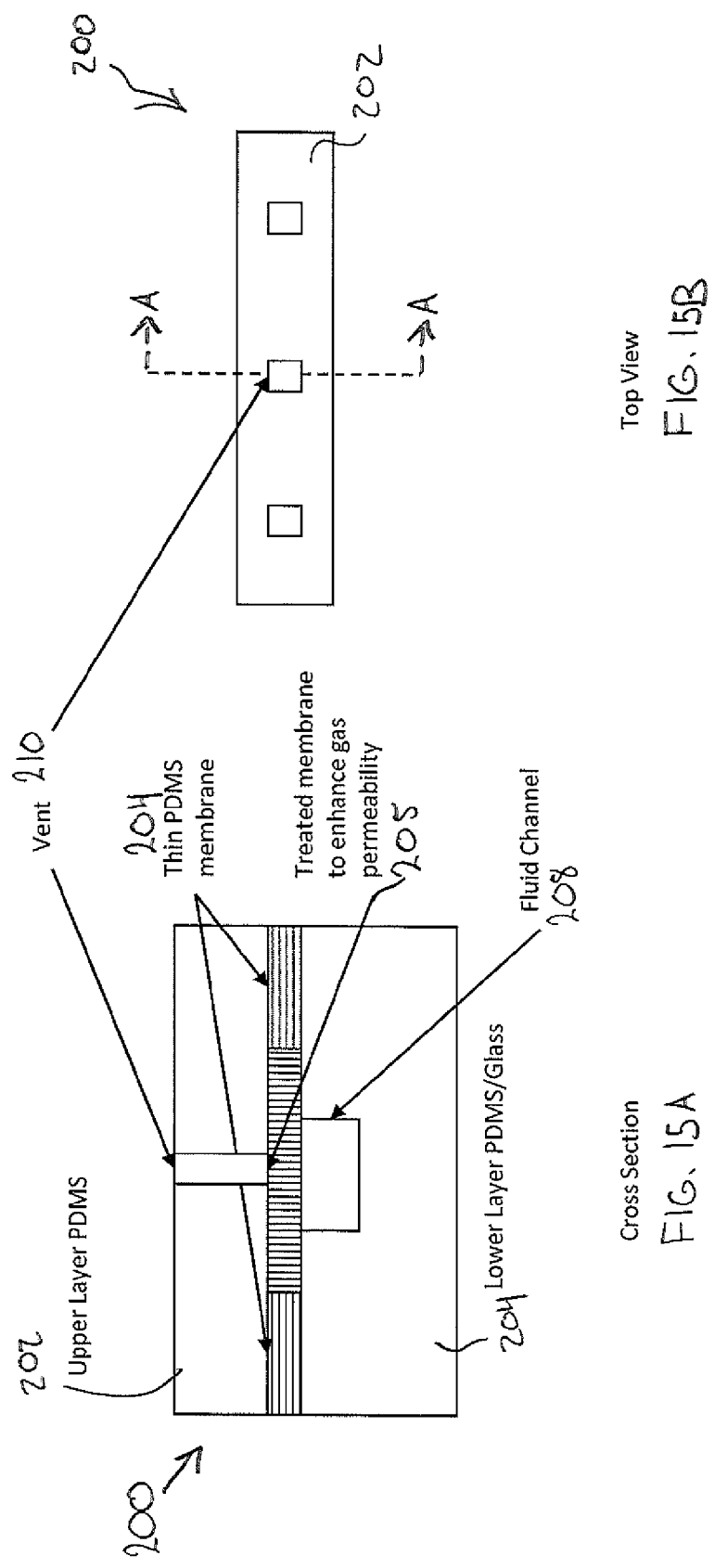
FIG. 15A shows a cross section of an alternative embodiment of the LoC arrangement of FIG. 14A with vents at multiple locations in the fluidic channel, where the vents expel air perpendicular to fluid flow, thereby allowing air bubbles between fluids to escape.
FIG. 15B shows a top view of the LoC of FIG. 15A with the cross-sectional position of FIG. 15A represented in dashed lines.

FIG. 15A shows a modified version of the fluidic LoC of FIG. 14A to include a number of vents 210 provided at multiple locations perpendicular to the fluid channel 208. The vents are provided as holes that extend through the upper layer 202 and serve as air passages out of the channel 208. The thin PDMS membrane 204 may be treated at locations 205 connected to the vents 210 in order to enhance gas permeability through the membrane 204. Thus, the thin PDMS membrane is configured to allow air to escape through the membrane at locations 205 while blocking the passage of liquids at these locations. The permeability of the membrane at the vent locations 205 can be altered by chemically modifying the PDMS membrane to make it thinner and more permeable. Any of various known methods may be used to modify the thickness, hardness/softness, or other properties of the PDMS membrane. In other embodiments, alternative materials may be used to achieve the desired functionality in the intermediate layer and vent locations.

Figure 16A:
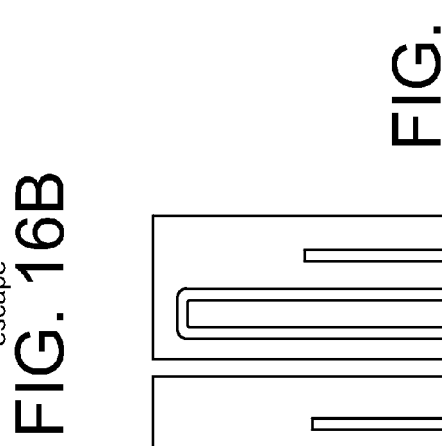
FIG. 16A shows a mixer channel configured to allow an air bubble escape from the channel sing the vent arrangement of FIG. 15A.
Figure 16B:
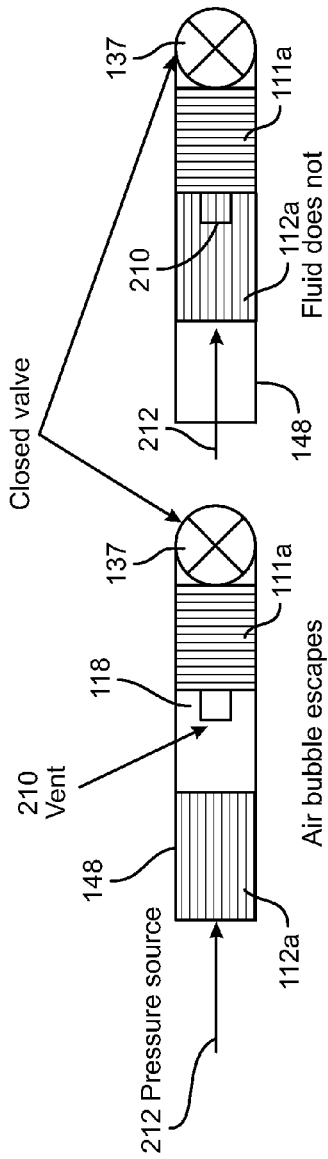
FIG. 16B shows the mixer channel of FIG. 16A with the air bubble forced out of the channel through the vent.
Figure 17:
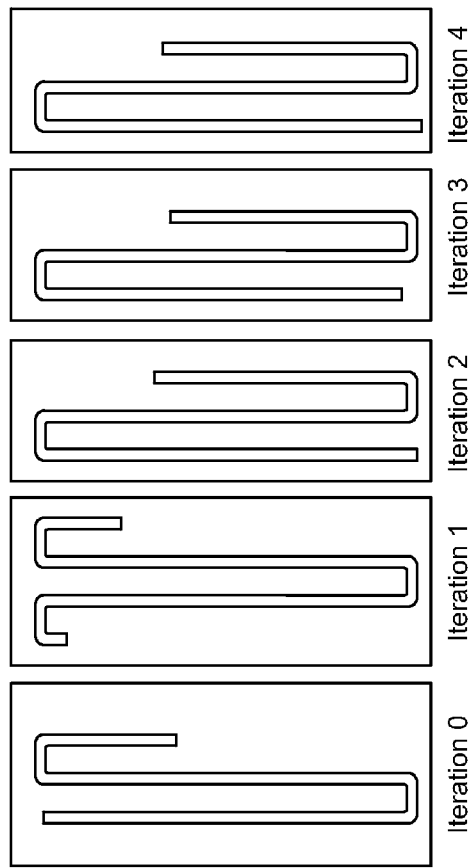
FIG. 17 shows the relationship between mixing efficiency and the number of mix iterations.

The embodiment of FIGS. 15A and 15B may be advantageously used in the mixing channel 144 in one of the above described embodiments of FIGS. 2-13. With the vents 210 of FIG. 15A positioned in the mixing channel 148, air bubbles may be easily passed out of the mixer 144. For example, as shown in FIG. 16A, in the event an air bubble 118 is trapped between two slugs (e.g., 111*a* and 112*a*) and is aligned below a vent 210, a closed valve 137 along with the application of pressure (e.g., by peristaltic pumping) can be used to remove the air bubble 118. In particular, the application of pressure (e.g., noted by arrow 212 in FIGS. 16A and 16B) forces slug 112*a* against the air bubble. Because slug 111*a* is prevented from further movement by closed valve 137, the air bubble 118 is forced out of the channel 148 through the gas-permeable membrane 205 and through the vent 210, as shown in FIG. 16B. Thus, the air bubble may be easily eliminated from the channel 148 using such vents 210. At the same time, liquids cannot escape though the vent 210 because while the gas-permeable membrane allows the passage of air and other gasses, it blocks the passage of liquid.

Mixing Efficiency

Figure 18:
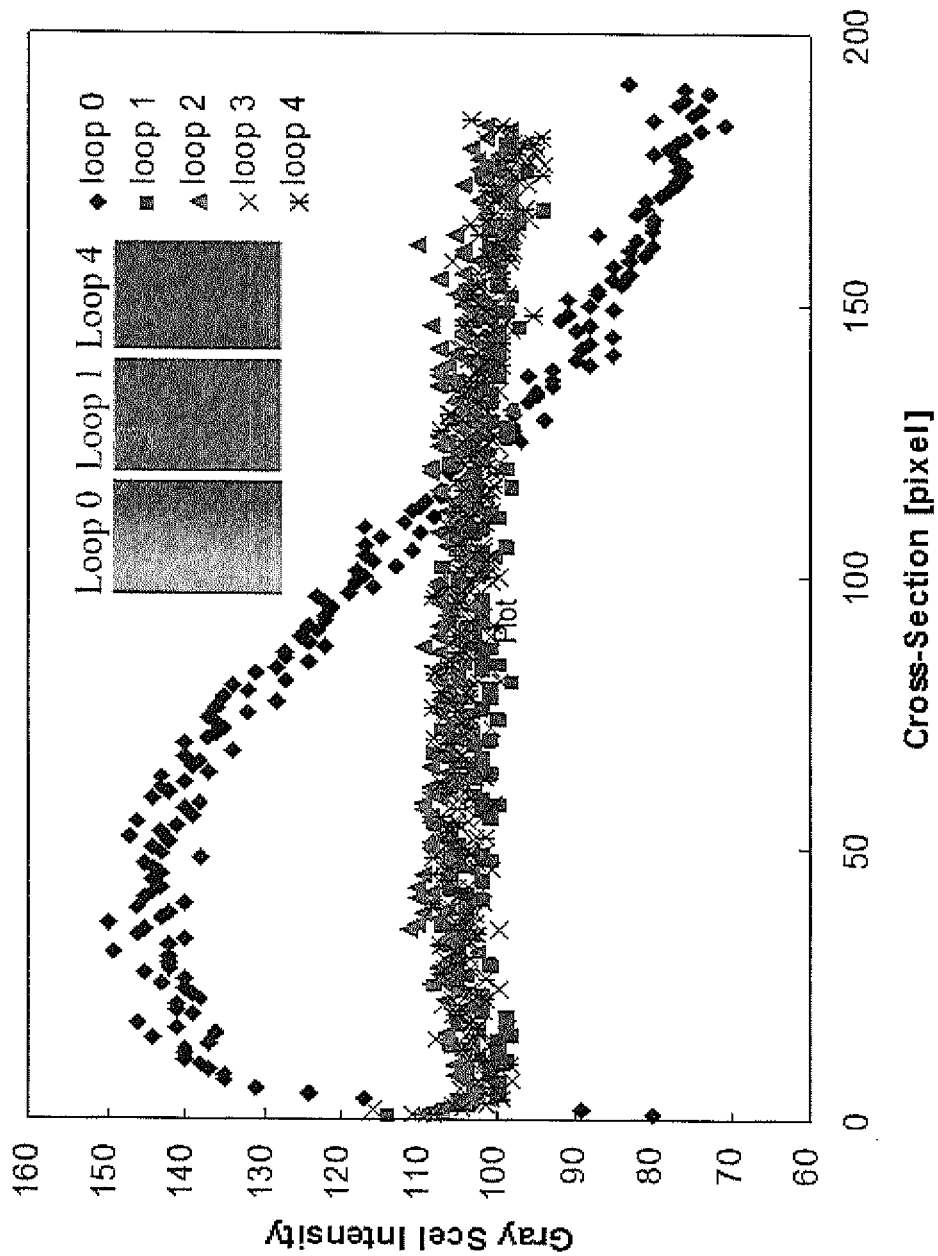
FIG. 18 is a graph of gray scale intensity at a cross section show in FIG. 17 as a function of number of mixing iterations.
Figure 19:
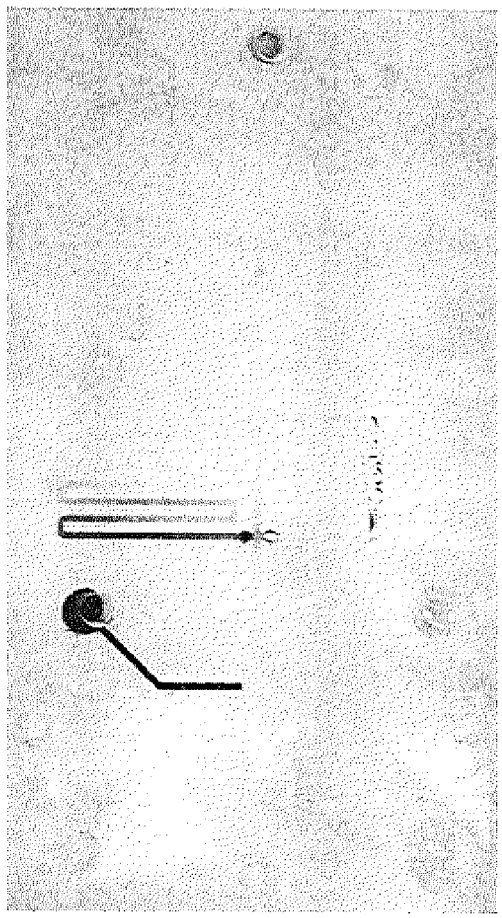
FIG. 19 is a photograph showing the mixing of a food coloring liquid and water.
Figure 20:
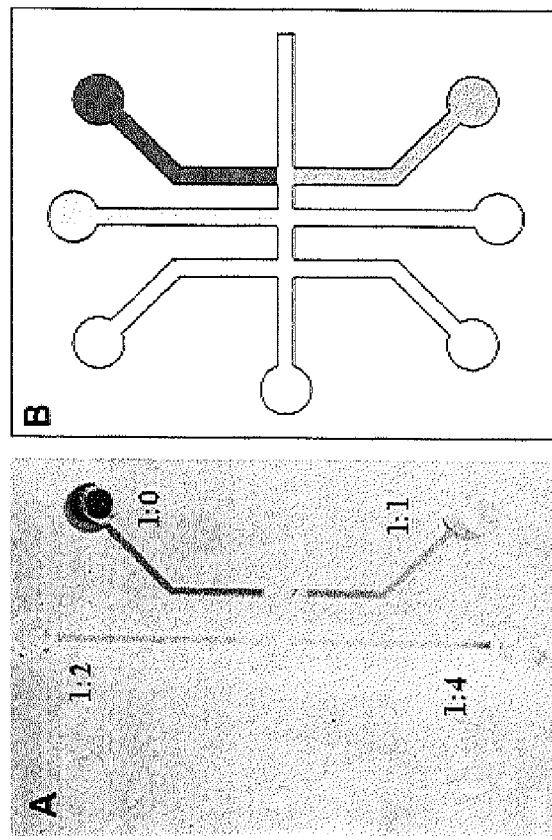
FIGS. 20A-20B show the result of mixing food coloring and water in different ratios (A) actual chip (B) expected output.
Figure 21:
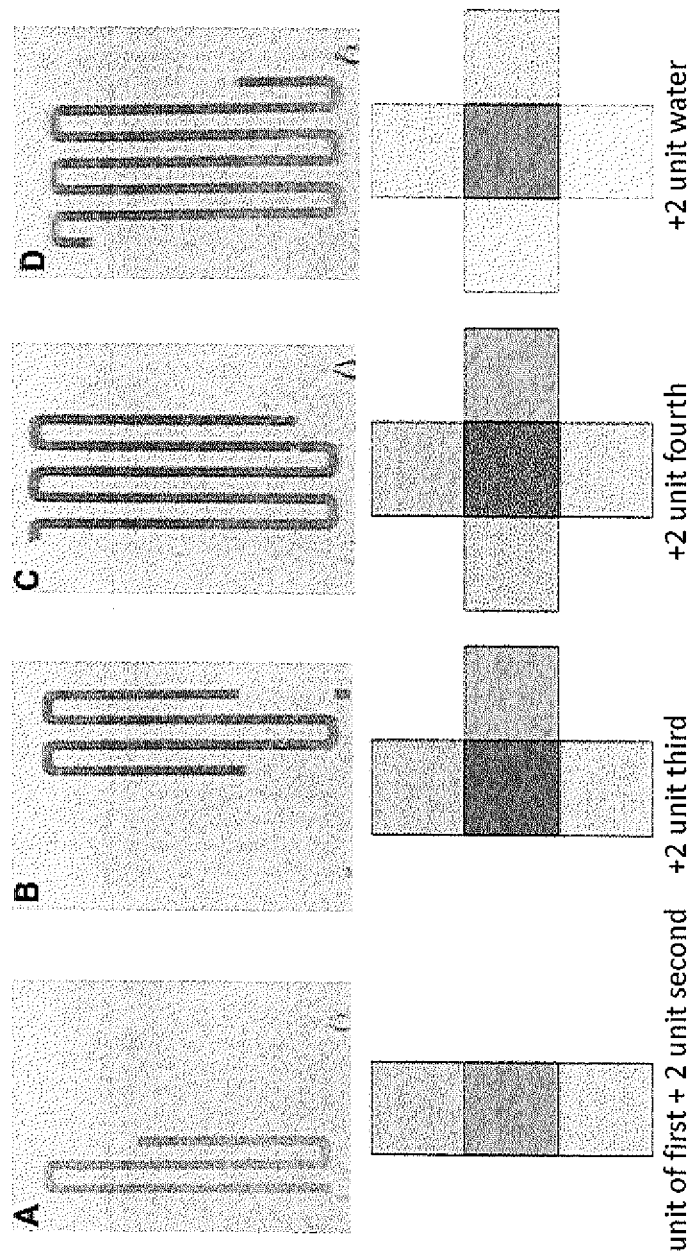
FIG. 21 shows the result of mixing of different food colorings in different volumes.

Referring now to FIGS. 17-21, mixing efficiency is demonstrated. FIG. 18 is a graph of gray scale intensity at a cross section show in FIG. 17 as a function of number of mixing iterations. The dotted line in FIG. 17 indicates where the gray scale intensity graph was taken. With respect to FIGS. 17 and 19-21, when mixing is not efficient, more than one shade of greyscale can be seen in the loop. The more mixing iterations, the more consistent the shading will be within the displayed loop. As shown in FIG. 18, loop 0 (before mixing) shows a significant curve, indicating a wide variation in grayscale. At the end of the mixing process (after loop 4), the line is very straight, indicating efficient mixing of the components.

Fluid Management System

In addition to the foregoing, the LoC arrangement disclosed herein provides a method for fluid volume management. As discussed previously, one challenge associated with fluid management is to ensure proper resource allocation such that volume distributions of a given fluid satisfy all of the proportions in a given assay mixing instruction. For instance, an assay may require mixing fluids A and B with a first ratio to produce fluid C. The assay may also require mixing fluids A and C with a second ratio to produce fluid D, which is later used to produce fluid E. Thus, volume distribution of fluid A among the various mixing operations should result in sufficient volume of D for its subsequent utilizations.

In order to ensure proper resource allocation, it is helpful to establish several constraints. First, an assigned volume of a fluid should not overflow or exceed the hardware capacity. The microfluidic system is defined by a series of channels, mixers, heaters, sensor units, etc. Each of these components has a maximum volumetric capacity. The volumetric capacity of the system may be defined by the smallest volumetric capacity of all the components.

A second constraint is that an assigned volume of a fluid should not underflow, i.e., fall below hardware transport resolution. The hardware transport resolution may be defined by the minimum amount of fluid that the smallest pump can drive per unit of time. For example, the resolution for a peristaltic pump is defined as the amount of fluid the pump drives each time the pump deforms an internal deformable bladder, as it is known in the art.

A third constraint is that fluid volumes should be integer multiples of the minimum hardware transport resolution. Violation of any of these constraints may result in the inability of the microfluidic system to properly and accurately mix and transport volumes of fluids throughout the system.

A linear programming (LP) approach, known in the art, may be used to allocate resources, e.g., volumes of fluids, to avoid violating the first and second constraints. To satisfy the third constraint an integer linear programming (ILP) approach is necessary. Alternatively, the LP approach can be used to satisfy the first two constraints followed by a rounding operation to achieve integers, in order to satisfy the third constraint. However, for L-bit of inputs and n variables, the LP approach has a worst-case asymptotic complexity of $O(n^3L)$. Such a complexity may be tolerable for small-size assays at compile-time. However, there may be cases where volumes of an intermediate fluid may not be available at compile time due to the volume being provided by a statically unknown step, e.g., an "if-then-else" construct, and thereby unavailable apriori. Therefore, the solution has to be calculated at run-time. In such cases, complexity of the LP approach may become prohibitive at run time. The ILP approach is even slower than the LP approach.

To address the complexity of the LP or the ILP approaches, a novel algorithm (hereinafter referred to as "the DAGSolve algorithm") with less complexity (linear complexity vs. cubic complexity) is described below. In addition a high level algorithm is also provided which uses the DAGSolve algorithm, and relies on the LP approach at run-time only if the DAG-Solve algorithm results in a violation of a constraint.

Table 1, below, provides mixing instructions for a simple assay program. Three inputs A, B, and C are used to generate two outputs M and N while producing two intermediate mixtures K and L.

TABLE 1

Mixing instruction for a simple assay

| Inputs: A, B, and C Fluid | Outputs: M and N Instruction | Ratio |
|---|---|---|
| K | mix A:B | 1:4 |
| L | mix B:C | 2:1 |
| M | mix K:L | 2:1 |
| N | mix L:C | 2:3 |

Figure 22:
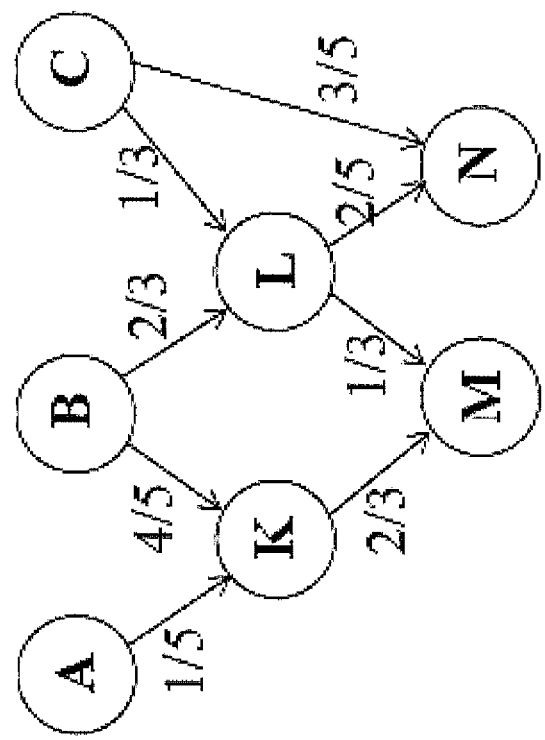
FIG. 22 shows a directed acyclic graph for an exemplary assay.

Referring to FIG. 22, a directed acyclic graph (DAG) is shown for the assay of Table 1. The DAG of FIG. 22 includes nodes and edges connecting the nodes. The nodes represent operations (typically volume-aggregating operations such as mixes) and edges represent dependence among the operations. The edges are annotated with values to denote the proportion of the source fluids that are used in the operation. There are three input nodes A, B, and C. There are two output nodes M and N, and there are two intermediate nodes K and L. The input nodes have no in-bound edges, while the output nodes have no out-bound edges. The edges are calculated based on the mixing instruction of the assay. For example, the intermediate node K is formed by a mixture of A and B with a ratio of one unit of A and four units of B. The contribution of A to K is ⅕ and the contribution of B is ⅘. While volumes of the edges are defined based on the assay's mixing instructions, the volume requirements of the input nodes and the volume produced at the output nodes are unknown. The DAG as is shown in FIG. 22 is the entry point into the DAGSolve algorithm or to another algorithm that uses the LP approach.

The DAGSolve Algorithm

The DAGSolve algorithm determines a solution for the assay by adding two additional constraints. First, the volumes of M and N are constrained to be in relative proportion to each other, e.g., $V_M:V_N$. The LP approach allows the outputs to be any volume. However, it should be appreciated that the new constraint does not fix the absolute volume of any output. Second, a flow-conservation constraint is also added. The flow conservation constraint forces the generated volume for each intermediate fluid, i.e., each node, to be equal to the total volume of outbound edges of the node.

Figure 23:
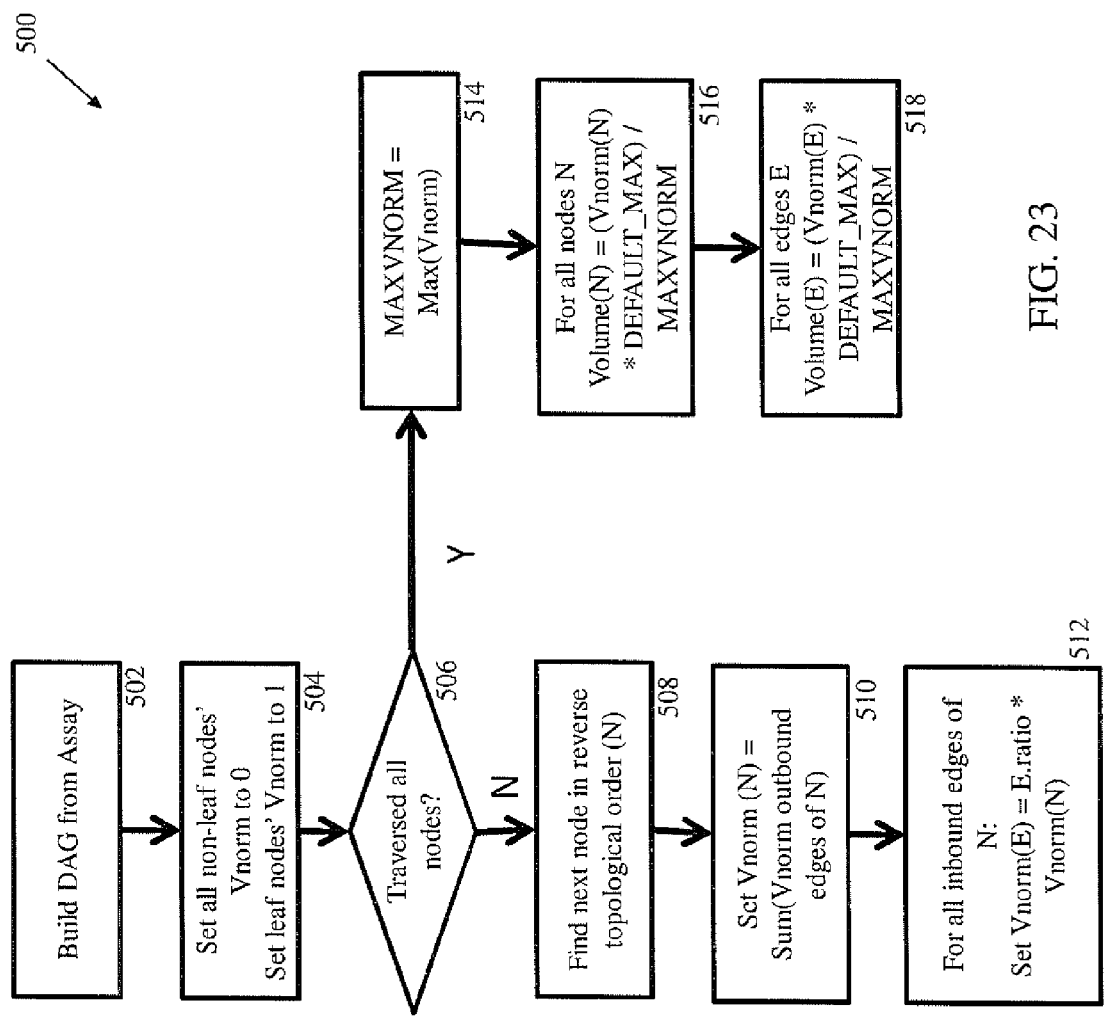
FIG. 23 shows a flowchart of at least one embodiment of an algorithm for determining fluid management for the directed acyclic graph of FIG. 22.

Referring to FIG. 23, a flowchart 500 of at least one embodiment of the DAGSolve algorithm is provided. The DAGSolve algorithm generates the DAG from the assay mixing instructions in step 502, if one has not already been generated. For example, the DAG of the assay that was described in table 1 is provided in FIG. 22. The algorithm then presets fluid volume of all non-output nodes (non-leaf nodes), i.e., nodes A, B, C, K, and L, to zero and presets the volumes of the leaf nodes, i.e., M and N, to one, in step 504. Therefore, in relationship to the DAG shown in FIG. 22, normalized volumes (Vnorm) of nodes A, B, C, K, and L are preset to zero, while normalized volumes (Vnorm) of nodes M and N are preset to one. The edges of the DAG which appear in FIG. 22 are temporarily maintained. A main loop begins with the query block 506, which queries whether all the nodes have been analyzed. The analysis of the nodes is performed in a reverse topological order, i.e., from bottom to top. If the answer to the query block 506 is no, then the next node in the reverse topological order is found, as shown in block 508. Thereafter, the volume of the node identified in block 508 is set to the sum of out-bound edges that leave the node, as shown in block 510. For example, for the node K, the volume is set to the sum of the out-bound edges that leave node K. The only edge that leaves K is ⅔, as shown in FIG. 22. Therefore, fluid volume of K is set to ⅔. However, node L has two out-bound edges leaving node L. These are ⅓ and ⅖. The sum of these two edges is 11/15, which becomes the fluid volume of node L.

With continued reference to FIG. 23, normalized volumes (Vnorm) of the in-bound edges of the node identified in block 508 are calculated by multiplying the volume of the node by the edge values of the old in-bound edges that are shown in FIG. 22, and as shown in block 512. For example, for node K, the inbound edges were ⅕ and ⅘, as shown in FIG. 22. The volume of inbound edges to node K is determined by multiplying the in-bound edges by the volume of node K, which is ⅔. Therefore, the new in-bound edges are 2/15 (⅔×⅕) and 8/15 (⅔×⅘). Similarly, for node L the volume of the old in-bound edges are ⅔ and ⅓. The volume of node L was determined to be 11/15 (⅓+⅖). Therefore, the volume of the new in-bound edges are 22/45 (⅔×11/15) and 11/45 (⅓×11/15). The loop of query 506 is repeated for nodes A, B, and C.

Figure 24:
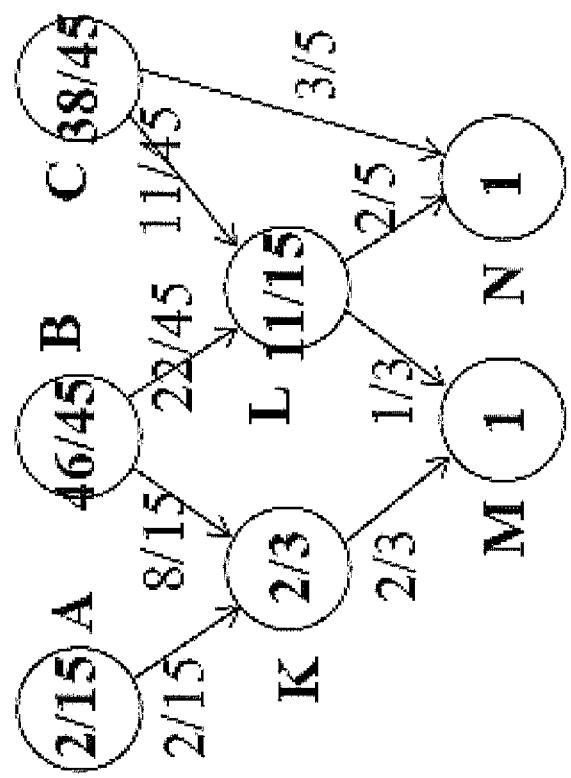
FIG. 24 shows a directed acyclic graph of the exemplary assay of FIG. 22 after traversing all of the nodes using the algorithm of FIG. 23.
Figure 25:
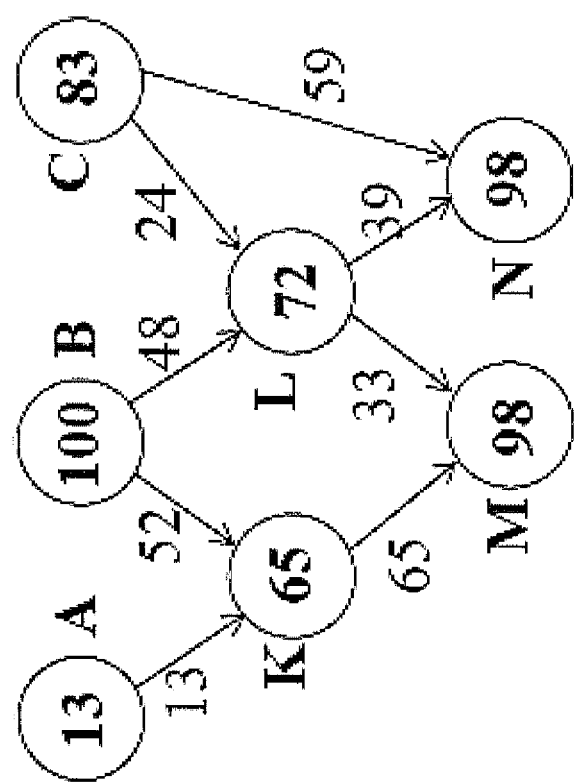
FIG. 25 shows a directed acyclic graph of the exemplary assay of FIG. 22 after performing the normalization section of the algorithm of FIG. 23.

Referring to FIG. 24, a DAG of the assay described in Table 1 is provided based on a solution that is arrived at by part of the DAGSolve algorithm, after traversing all of the nodes. As shown in FIG. 24, the volume of the leaf nodes, i.e., output nodes, is set to 1 and a volume for each of the remaining nodes is also determined, as described above. The remaining portion of the DAGSolve algorithm normalizes volumes of the nodes and edges based on the maximum volume. In the case of FIG. 24, the maximum volume is that of node B and is 46/45. Block 514 identifies the maximum volume. Block 516 normalizes node volumes based on the volume identified in block 514 by multiplying the volume of each node by a default maximum volume, e.g., 100 nL (which may be, for example, the volume of the largest fluid reservoir), and dividing by the maximum volume identified in block 514. The normalized node volume is then rounded down to the next lower integer. For example, normalized volume of node A is calculated by multiplying 2/15 by 100 and dividing by 46/45, and by rounding down to 13. Block 518 performs a similar function for edge volumes. For example, the normalized volume of the outbound edge of node K is determined by multiplying ⅔ by 100 and dividing by 46/45, and by rounding down to 65. FIG. 25 is a DAG of the assay described in Table 1 after performing the normalization section of the DAGSolve algorithm.

While the DAGSolve algorithm provides a linear algorithm complexity as compared to a cubic complexity for the case of the LP approach, making use of the algorithm a preferred choice, in rare instances the algorithm may cause violation of one of the constraints. In such a case, the LP approach may be used to solve for the node and edge volumes.

However there are corner cases, such as extreme mix ratios (e.g., mix ratio of 1:1000) or numerous uses of a fluid (e.g., 7 uses of a fluid that has a volume of 6 multiples of minimum hardware transport resolution), that can cause both the LP approach and the DAGSolve algorithm to violate one of the constraints. For instance, a mix ratio of 1:399 using hardware with maximum and minimum capacities of 100 and 1 units, respectively, would cause either an underflow or an overflow. To handle such extreme ratios, a cascading approach is used to break the extreme ratio into two or more cascaded ratios. For example, the extreme ratio of 1:399 can be realized by providing a first ratio of 1:19, and then by providing a second ratio of 1:19 based on the first ration of 1:19 ($\frac{1}{19} \times \frac{1}{19}$). This method is hereinafter referred to as the cascading approach. Also, because of hardware limits of maximum capacity, numerous uses of a fluid can cause an underflow condition, even if as much volume of the fluid is provided as possible without causing an overflow condition. In such cases, extra volumes are provided by replicating portions of the assay. This method is hereinafter referred to as the static replication approach.

Figure 26:
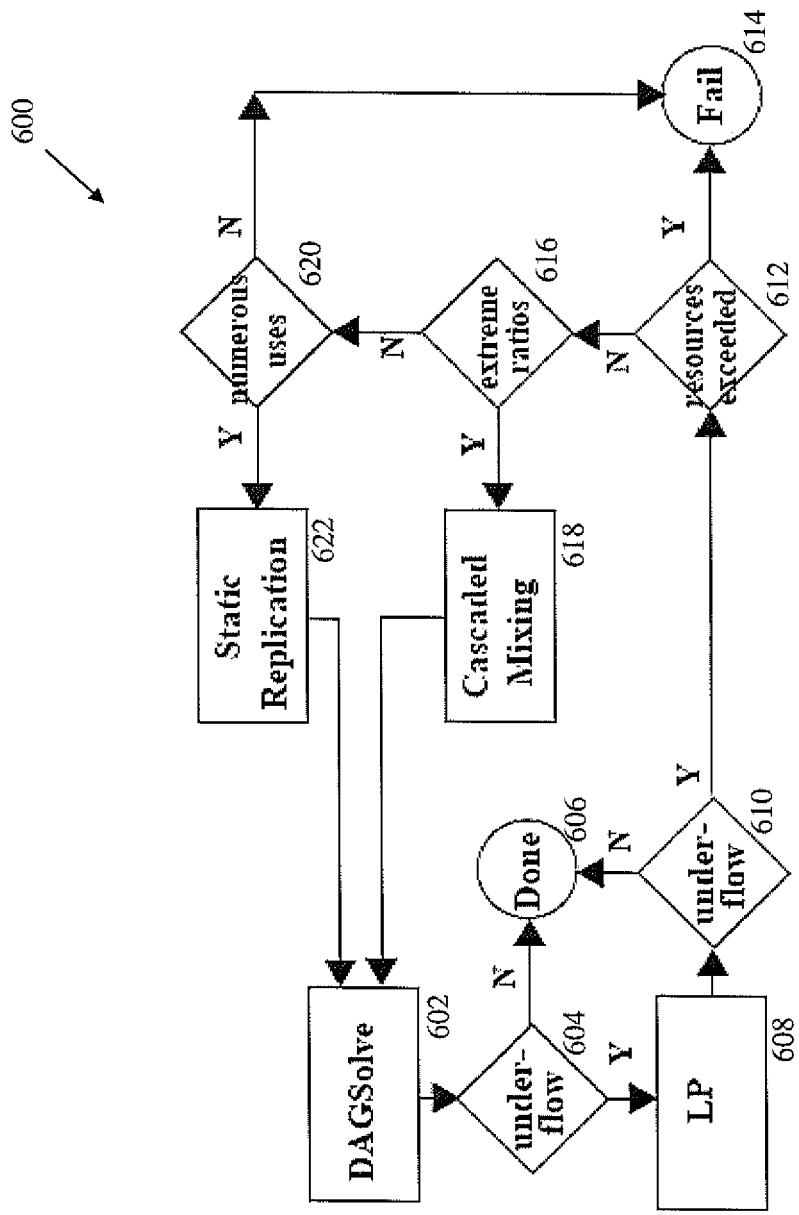
FIG. 26 shows a flow chart of a volume management system that includes an alternative embodiment of the algorithm of FIG. 23.

Referring to FIG. 26, a flow chart of the volume management system 600 is provided that includes running the DAGSolve algorithm and applying the LP approach, in an alternative manner, to the mixing instructions. The flow chart shown in FIG. 26 initially attempts to use the algorithm to solve for node and edge volumes, as shown in a block 602. After applying the algorithm, the volume management system 600 checks for any violations of the underflow constraints, as shown in a query 604. If there are no violations, then the volume calculation is complete and the system 600 arrives at a state 606. However, if there is a constraint violation, the system 600 applies the LP approach, as shown in a block 608. Once again, the system 600 checks for constraint violation, as shown in a query 610. If there are no violations, then the system 600 arrives at the state 606. However, if there is a violation, the system 600 checks to determine whether resources were exceeded, e.g., all reservoirs and fluid channels have been assigned, as shown in a query 612. If the resources are exceeded, then the system arrives at a state 614 which indicates a compilation failure. However, if the resources were not exceeded, the system 600 checks to determine if there is an extreme ratio included in the mixing instructions, as indicated by a query 616. If the system determines there is an extreme ratio, then the system performs a cascading operation based on the cascading approach, discussed below, to replace the extreme ratio portion of the mixing instructions, as shown in a block 618.

After the cascading operation (block 618) is complete, the system 600 returns to the DAGSolve algorithm to try to solve for the node and edge volumes again. However, if the system 600 determines there are no extreme ratios, the system 600 checks to determine if there is a case of numerous uses of a fluid in the mixing instructions, as indicated by a query 620. If the system determines there is a case of numerous uses, then the system performs a static replication operation based on the static replication approach, discussed below, as shown in a block 622. Once the static replication operation is complete, the system 600 returns to the DAGSolve algorithm to solve for the node and edge volumes again. However, if the system 600 determines there is no case of numerous uses then the system arrives at the state 614.

The Cascading Operation

The cascading operation includes breaking an extreme ratio into smaller ratios. In general the cascading operation is performed when no feasible volume assignment can be determined using direct mixing as provided in the assay mixing instructions. When an extreme mix ratio 1:R, e.g., 1:399 is encountered by the system 600, initially the system attempts a cascade of two mixes, where each mix is equivalent to 1:$\sqrt{R+1}-1$, e.g., 1:19 and where an amount of discarded fluid at the intermediate node is $\sqrt{R+1}-1/\sqrt{R+1}$, $\frac{19}{20}$. If one level of cascading is insufficient to eliminate the extreme mix ratio, the system 600 iteratively deepens the cascading by using three mixes each equal to 1:

$$1:\sqrt[3]{R+1}-1$$

and so on, until a suitable non-extreme mix-ratio is achieved. The reader should appreciate that cascading has the negative side-effect of increasing demand on the fluid resources due to generating waste. In extreme cases, cascading may cause a violation of the underflow constraint.

The Static Replication Operation

The static replication operation (block 622) includes proactive generation of fluid in excess of what a single reservoir can hold by providing multiple instances of the same fluid. A numerous-usage node is replicated and which can distribute the original outbound fluid uses as evenly as possible between the replicas. Once replication is complete, the DAGSolve algorithm is executed to determine new volumes for the nodes and the edges. If an underflow occurs again, a second replication level is provided in the DAG. Replication continues in an iterative fashion until the underflow is eliminated. Because replication increases the demand on the fluid-path resources (similar to cascading), the replicated code may exceed the resources of the microfluidic system. In such cases, compilation fails.

Statically Unknown Solutions

The DAGSolve algorithm discussed thus far has been based on statically known volumes for the outputs and known number of uses of a fluid in every step of the DAG. In statically known situations, the entire DAG can be solved at compile time to arrive at a statically known solution. However, there may be cases where certain parameters are only known at run time. In accordance with at least one embodiment, to handle statically-unknown volume cases, e.g., due to a step where the volume of a node is unknown, the volume normalization steps in the DAGSolve algorithm are delayed from compile time to run time while maintaining volume calculation steps at compile time to reduce run-time overhead. To compute volumes, the outbound edges of the unknown-volume nodes, are deleted. Consequently, these nodes become similar to final output nodes (leaf nodes), while a sink node of each deleted edge becomes similar to an input node. However, there is a difference between a sink node and an input node. While volume of an input node is unconstrained up to the default maximum, a sink node volume is constrained to be equal to the output of the unknown-volume instruction. This volume is measured at run time.

The edge deletion may partition the DAG into several sections. The DAGSolve algorithm is applied to each section. Volume of each node and edge of each section is calculated, as discussed above. However, there is one difference in the final step of normalized volume assignment. Assigning the default maximum to the node with the largest volume may require more than the available volume at a constrained input in one of the sections. To handle such a case, the minimum ratio of each input's volume and the available input volume for each constrained input once the volume is measured is calculated. Consequently, nodes and edges are assigned volumes by scaling their volumes with this ratio.

Examples of statically unknown cases are "loops" and "if-then-else" constructs in the mixing instructions. To handle if-then-else constructs, both "if" and "else" paths are includes in the DAG. The DAGSolve algorithm is then applied to both paths. Loops with statically-known number of iterations can be unrolled and solved by the DAGSolve algorithm. For loops with unknown number of iterations at loop entry (e.g., "while" loops), there are two options: (1) The programmer provides a hint of the upper bound on the number of iterations for a loop, the loop is deconstructed as many times and the DAGSolve algorithm applied thereto. (2) While the programmer may not know the number of iterations, the minimum volumes that the loop should output for successful completion of the assay may be known. These minimum volumes can be used in the case of loops with independent iterations. For such loops, two changes are made to the DAGSolve algorithm before applying it to the loop body. First, instead of assigning the largest volume to the default maximum, the output node with the smallest volume is identified and is assign as the programmer-specified volume. All other nodes and edges are scaled as per the ratio of their volume and that of the chosen output node. This process provides the volumes of the input fluids needed for one iteration in order to produce the specified output volumes in that iteration. This strategy, however, is a departure from the flow-conservation constraint of the DAGSolve algorithm where an intermediate node produces only as much fluid as is needed. Accordingly, the second change is that the assay is broken up at the entry to loops. The nodes outputting fluids to the loops are thus treated as if they were final output nodes.

The per-iteration input volumes are valid only if the loop iterations are independent. In the presence of loop-carried dependencies, the specified output volumes would be reached after multiple iterations. As such, input volumes cannot be calculated from one iteration, as discussed above. For such loops, the DAGSolve algorithm falls back on the first option of the programmer specifying an upper bound on the number of iterations. The reader should appreciate that the programmer-provided hints or bounds could be from any source including but not limited to human expertise, profiling runs, and prediction.

Those skilled in the art will recognize that numerous modifications can be made to the specific implementations described above. Therefore, the following claims are not to be limited to the specific embodiments illustrated and described above. The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

What is claimed is:

1. A programmable lab-on-a-chip (PLoC) arrangement, comprising:
    a fluid channel configured to receive a first fluid from a first inlet and a second fluid from a second inlet;
    a mixer connected to the fluid channel, the mixer including a mixer channel configured to receive a volume of the first fluid and a volume of the second fluid from the fluid channel, the mixer channel defining a mixer capacity, wherein the mixer is (i) configured to mix the volume of the first fluid and the volume of the second fluid in order to provide a mixture of the first fluid and the second fluid when the combined volume of the first fluid and the second fluid is less than the mixer capacity, and (ii) further configured to mix the volume of the first fluid and the volume of the second fluid in order to provide a mixture of the first fluid and the second fluid when the combined volume of the first fluid and the second fluid is equal to the mixer capacity; and
    an air purging arrangement disposed in the mixer channel and configured to purge a volume of air from the mixer channel when the volume of air is positioned between the volume of the first fluid and the volume of the second fluid in the mixer channel, the air purging arrangement including a vent orthogonally oriented to a direction of flow of the fluids in the PLoC and including a membrane configured to allow passage of gas and block passage of liquids.

2. The PLoC arrangement of claim 1 further comprising a pump configured to meter the first fluid and the second fluid into the fluid channel.

3. The PLoC arrangement of claim 2 wherein the pump is positioned in the fluid channel.

4. The PLoC arrangement of claim 2 wherein the pump is a first pump, the PLoC arrangement further comprising a second pump positioned in the mixer channel.

5. The PLoC arrangement of claim 1 further comprising an outlet in the fluid channel, the outlet configured to release the mixture from the fluid channel.

6. The PLoC arrangement of claim 1 wherein the membrane is a PDMS material.

7. The PLoC arrangement of claim 1 further comprising a sensor configured to sense when the volume of the first fluid is in a predetermined position.

8. The PLoC arrangement of claim 1 further comprising a plurality of valves positioned in the fluid channel, wherein plurality of valves are automatically controlled along with the pump in order to transport the first fluid and the second fluid to various locations within the PLoC.

9. A method of mixing a first fluid and a second fluid in a programmable lab-on-a-chip (PLoC) arrangement, the method comprising:
    transporting a first fluid to a mixer in the PLoC arrangement, the mixer having a mixer channel defining a mixer capacity;
    sensing the position of a second fluid at an entrance to the mixer before transporting the second fluid to the mixer;
    transporting the second fluid to the mixer, wherein the total combined volume of the first fluid and the second fluid is less than the mixer capacity;
    mixing the first fluid and the second fluid within the mixer channel into a mixture of the first fluid and the second fluid; and
    automatically determining the volume of the first fluid and the volume of the second fluid for transporting based on an assay program comprising a plurality of assay instructions, the assay instructions identifying a plurality of input fluids, a plurality of output fluids, and mixing proportions for the input fluids and any intermediate fluids for generating the output fluids,
    wherein the assay instructions may be characterized as a directed acyclic graph including a plurality of leaf nodes and a plurality of non-leaf nodes with outbound edges, and wherein each outbound edge of each non-leaf node is assigned a value associated with one of the mixing proportions from the assay instructions, and wherein automatically determining comprises determining volume ratios for the non-leaf nodes in reverse topological order, wherein the volume ratio of each non-leaf node is equal to the sum of the values of the outbound edges of said non-leaf node, and wherein the value assigned to the outbound edge of a non-leaf node is re-assigned when the volume ratio of a node to which the outbound edge leads is determined, wherein the reassigned value of the outbound edge is equal to the previous value assigned to the outbound edge times the volume ratio of the node to which the outbound edge leads.

10. The method of claim 9 further comprising metering the first fluid and the second fluid using a peristaltic pump before transporting the first fluid and the second fluid into the mixer, and wherein mixing the first fluid and the second fluid includes pumping the first fluid and the second fluid within the mixer channel.

11. The method of claim 10 further comprising sensing the second fluid at an entrance to the mixer before operating the pump.

12. The method of claim 9 wherein transporting the first fluid comprises pumping the first fluid to the mixer from a first fluid source using a peristaltic pump.

13. The method of claim 9 further comprising purging air bubbles from the mixer channel through vents in the mixer channel.

14. The method of claim 9 further comprising transporting the mixture from the mixer to a fluid outlet of the PLoC arrangement or a reservoir.

15. A method for managing fluid resources in a microfluidic system, the method comprising:
receiving assay instructions identifying input fluids, output fluids, and mixing proportions used to generate said output fluids from said input fluids;
generating a data stream corresponding to nodes and edges of a directed acyclic graph representing said received assay instructions, said nodes defining fluid operations, said edges defining interdependence between said nodes; and
presetting data values of said data stream corresponding to said edges based on said mixing proportions.

16. The method of claim 15, further comprising:
presetting data values of said data stream corresponding to non-output nodes to zero and presetting data values of said data stream corresponding to output nodes to a predetermined value;
identifying data entry corresponding to each of said non-output nodes in said data stream in a bottom-up manner;
summing said data values corresponding to outbound edges of said identified data entry corresponding to each of said non-output nodes to generate a calculated data value corresponding to each of said non-output nodes; and
multiplying said data value corresponding to an inbound edge of said identified data entry corresponding to each of said non-output nodes by said calculated data value corresponding to each of said non-output nodes to generate a calculated data value corresponding to said inbound edge.

* * * * *